US009802739B2

United States Patent
Oldani et al.

(10) Patent No.: US 9,802,739 B2
(45) Date of Patent: Oct. 31, 2017

(54) HEAT TRANSFER APPARATUS AND CONTAINER

(75) Inventors: Charmayne Oldani, Queanbeyan (AU); David John Bull, Riverview (AU); Andrew Richard Wyatt, Chatswood (AU); Michael John Batty, North Epping (AU); Peter Charles Spencer, Coogee (AD); Sandy McNeil, Gladesville (AU)

(73) Assignee: Kismet Design Pty Ltd, Queanbeyan (AU)

( * ) Notice: Subject to any disclaimer, the term of this patent is extended or adjusted under 35 U.S.C. 154(b) by 975 days.

(21) Appl. No.: 13/698,131

(22) PCT Filed: May 19, 2011

(86) PCT No.: PCT/AU2011/000596
§ 371 (c)(1),
(2), (4) Date: Nov. 15, 2012

(87) PCT Pub. No.: WO2011/143713
PCT Pub. Date: Nov. 24, 2011

(65) Prior Publication Data
US 2013/0059259 A1    Mar. 7, 2013

(30) Foreign Application Priority Data

May 19, 2010 (AU) ................................ 2010902176

(51) Int. Cl.
*F27D 21/00* (2006.01)
*B65D 51/18* (2006.01)
(Continued)

(52) U.S. Cl.
CPC ........... *B65D 51/24* (2013.01); *A47J 36/2411* (2013.01); *A61M 5/44* (2013.01); *B65D 51/18* (2013.01);
(Continued)

(58) Field of Classification Search
CPC .. F23D 21/00; F23D 99/00; F23C 5/02; A47J 36/2483; A47J 36/2461; A47J 36/2433;
(Continued)

(56) References Cited

U.S. PATENT DOCUMENTS 2,470,806 A * 5/1949 Del Cueto .......... A47J 36/2483
215/376
3,733,771 A   5/1973 Megowen
(Continued)

FOREIGN PATENT DOCUMENTS

DE   10327495 B4 * 7/2007 .......... A47J 36/2483
FR   2752377 A1 * 2/1998 .......... A47J 36/2433

OTHER PUBLICATIONS

PCT International Preliminary Report on Patentability for PCT/AU2011/000596 dated Mar. 19, 2012.

*Primary Examiner* — Steven B McAllister
*Assistant Examiner* — Steven Anderson, II
(74) *Attorney, Agent, or Firm* — Shaukat A. Karjeker; Carstens & Cahoon, LLP

(57) ABSTRACT

A container for holding liquid is described. The container defines an inner region inside which liquid is adapted to be held and includes one or more walls for facilitating heating or cooling of the liquid therethrough, the one or more walls being adapted for invagination by a temperature control probe such that the temperature control probe extends into the container without directly contacting contents of the inner region of the container.

14 Claims, 9 Drawing Sheets

(51) Int. Cl.
*B65D 51/24* (2006.01)
*A47J 36/24* (2006.01)
*B65D 81/34* (2006.01)
*A61M 5/44* (2006.01)
*A61J 1/10* (2006.01)
*A61J 9/00* (2006.01)

(52) U.S. Cl.
CPC ............... *B65D 81/34* (2013.01); *A61J 1/10* (2013.01); *A61J 9/00* (2013.01); *A61J 2200/42* (2013.01)

(58) Field of Classification Search
CPC .......... A47J 36/2411; A61J 9/00; A61M 5/44; B65D 51/24; B65D 51/34; B65D 51/18
See application file for complete search history.

(56) References Cited

U.S. PATENT DOCUMENTS

| | | | |
|---|---|---|---|
| 4,008,820 A | 2/1977 | Ruetz | |
| 4,886,177 A | 12/1989 | Foster | |
| 5,284,028 A | 2/1994 | Stuhmer | |
| 5,456,090 A * | 10/1995 | McCoy | A61J 9/00 165/80.5 |
| 5,467,877 A | 11/1995 | Smith | |
| 6,415,624 B1 | 7/2002 | Connors et al. | |
| 7,082,784 B2 * | 8/2006 | Roth | A45F 3/16 220/23.87 |
| 7,166,822 B1 * | 1/2007 | Chang | A47J 27/022 219/430 |
| 7,287,656 B2 | 10/2007 | Guilford, III et al. | |
| 2006/0231519 A1 * | 10/2006 | Py | B65D 51/002 215/342 |
| 2009/0236334 A1 * | 9/2009 | Ben-Shmuel | B65D 81/3453 219/703 |
| 2009/0236335 A1 * | 9/2009 | Ben-Shmuel | H05B 6/6402 219/710 |

\* cited by examiner

HEAT TRANSFER APPARATUS AND CONTAINER

FIELD OF THE INVENTION

The present invention relates to temperature control of a liquid, and, in particular, to the heating and/or cooling of a selected volume of liquid. The present invention also relates to heat transfer apparatus including closures and containers suitable for facilitating heat transfer, as well as methods for heating liquids, and liquid heating apparatus.

BACKGROUND OF THE INVENTION

There are a number of liquids that are stored at cold temperatures but require heating or warming before use. Examples include breast milk or infant formula for feeding babies and whole blood, plasma or serum for use in transfusion or infusion of patients. In both situations, it is important to heat or warm the liquid to a desired temperature, typically around 37° C., without overheating or uneven heating.

Breast milk or formula is generally stored in a refrigerator and heated from a storage temperature of about 4° C. to a body temperature of approximately 37° C. before being fed to the newborn baby. Lower heated milk or liquid feeding temperatures may be used in cases where parents are weaning their infants from a reliance on warmed milk or liquid.

One method of heating breast milk or formula is to use a microwave oven. However, microwave heating is known to result in hot spots within the volume of the liquid during the heating process. This can in turn lead to denaturing of nutrients present in milk.

Another method of heating breast milk or formula is to place a baby bottle containing the baby milk in an insulated cup containing hot water. This method of heating is generally slow since the walls of the baby bottle are usually bad conductors of heat. Furthermore, additional time and energy is required for heating of the water before the milk can be heated.

The methods of heating mentioned above are also not suitable when travelling or in remote areas such as battlezones or refugee areas, where access to appliances, work spaces and power is restricted. Additionally, both methods of heating require an approximation or manual measurement of the temperature of the liquid during heating.

Another type of liquid that requires heating before use is medical liquid for infusion such as for example blood, plasma or serum. Like milk, blood is generally stored at a temperature of approximately 4° C. Prior to use, the blood should be heated to body temperature of about 37° C. It is preferable that blood or plasma products be heated to body temperature as quickly as possible. It is also preferable for the blood heating system to be simple and straightforward to use. Some of these plasma products or other blood products can be frozen or partially frozen in storage.

Blood and blood products are often required in mobile hospitals, for example in battleground situations or refugee camps where power supplies are unpredictable and sometimes non-existent.

Another system of heating blood uses a heat exchanger coupled with two pumps. Blood and a suitable heat transfer liquid such as water are continuously pumped through the heat exchanger, wherein the water is separated from the blood but in heat transfer relationship therewith. The water is heated externally of the heat exchanger to maintain the blood at a preset desired temperature. This method of heating is generally not suited for outdoor conditions since the heat exchanger is bulky and difficult to operate.

Further, it is necessary at times to cool hot liquids quickly without liquid in certain zones being changed in state from liquid to solid.

The present invention seeks to provide a new heat exchange apparatus and method for heating or warming liquids.

It is to be understood that, if any prior art information is referred to herein, such reference does not constitute an admission that the information forms part of the common general knowledge in the art, in Australia or any other country.

SUMMARY OF THE INVENTION

In a general aspect, the present invention relates to heating or cooling of fluid disposed inside a container by a probe extending inside the container without the probe making direct contact with the fluid inside the container.

In accordance with a first aspect of the present invention there is provided a closure for a container, the closure comprising:

an engagement portion to sealingly engage an opening region of a container; and a crown portion including an inner surface adjacent to an inner region of the container and an outer surface opposed to the inner surface, the crown portion attached to or integral with the engagement portion and adapted to form a recess which extends into the inner region of the container to facilitate heat transfer to or from contents of the container.

Advantageously, the crown portion functions as a heat transfer device that enables heat to be transferred from the temperature control probe to a liquid which in use may be disposed in the container.

The crown portion may be a panel or other surface which extends to cover the opening region of the container between edge regions of the engagement portion.

Advantageously, the engagement portion facilitates use of the closure as a closure for sealing the liquid in the container for purposes other than heat transfer, such as storage or transport of the liquid. Sealing the liquid in the container is further beneficial, for example, in preventing spillage of the liquid during heating. As a result of the liquid being sealed, it is possible, for example, to substantially orient the container such that the crown is below the container, and correspondingly, the liquid is located above the crown in use. This ensures that the liquid makes contact with the crown even when the container is not completely filled by the liquid. Additionally, having the liquid located above the crown enables more convection within the liquid than, for example, having the liquid located below the crown during heat transfer, in use. Convection increases the rate of heat transfer from the crown to the liquid, and further inhibits inadvertent overheating of the liquid in contact with the second surface area of the crown portion during heat transfer.

Advantageously, the crown portion of the closure allows the liquid in the container to be heated without the need for prior removal of the crown, and insertion of, for example, a temperature control probe into the container. This inhibits the liquid in the container from becoming contaminated due to, for example, contact with the temperature control probe. This is further beneficial in affording user convenience since the closure does not need to be removed, for example, until the liquid in the container is heated and ready to be used.

Advantageously, the direct contact between the outer surface area of the crown of the closure and the liquid improves the efficiency of heat transfer from the crown to the liquid.

Preferably an overcap is provided to facilitate improved engagement with the opening region of the container.

Preferably, the crown portion is removably connected to the overcap.

Advantageously, the crown may be removed from the overcap such that the crown and the overcap can be subjected to separate treatments, (for instance, sterilization) or can be disposed of separately.

Advantageously, the crown portion and the overcap may be made from different materials according to their respective functions. For example, the crown portion may be made from one or more materials with good thermal conductivity such that the crown portion may transfer heat efficiently and promptly, and the overcap may be made of one or more materials with good sealing properties and good temperature resistance such that the overcap may facilitate effective sealing of the liquid in the container, and further be cool to the touch immediately after heat transfer, respectively.

Preferably, the crown portion comprises one or more projections that function to increase the total heat transfer surface area. Preferably the crown portion includes major projections such that the crown portion extends into the container for improved heat transfer and forms the recess. The recess may be thought of as an invagination which is either formed when a temperature probe is inserted into the crown portion and extended to an interior volume of the container, or a pre-formed invagination or recess cooperating in geometry and size with the temperature probe, into which the temperature probe may be easily inserted.

Preferably the crown portion includes minor projections in such an arrangement as a plurality of heat sink fins or for example villi of a stomach or small intestine which also increase the surface area for facilitation of heat transfer between liquid content and the crown portion. Advantageously, the rate of heat transfer, being directly proportional to the total heat transfer area, is correspondingly increased. This is beneficial, for example, in instances wherein the liquid to be heated may not be subject to a large temperature gradient that will increase the rate of heat transfer during the heat transfer process. An example of such a liquid is milk, wherein the substantial amounts of proteins or other nutrients contained in the milk may be denatured when the liquid is exposed to high temperatures for a period of time such as that in excess of approximately 60° C. to 70° C. In these instances, the increased total heat transfer surface area aids in minimising the time taken for the liquid to be heated.

Preferably, the closure and/or the overcap further comprises a tamper evident portion.

Advantageously, the tamper evident portion allows the integrity of the liquid in the container to be guaranteed. This is particularly beneficial where the heat transfer cap is used in combination with a single use pre mixed baby milk or liquid container product.

In some embodiments, the crown may be made from one or more materials selected from a polymer, a ceramic, a glass, a substantially non-corroding metal, or a combination thereof.

Advantageously, the one or more non-corroding materials prevent contamination of the liquid in the container.

Preferably, the crown portion is made of one or more flexible materials such that the crown portion is collapsible. In some embodiments the crown portion is a flexible and resilient membrane, between about 0.5 mm thick and 10 mm thick. Also, the membrane may be about 1 mm, 2 mm, 3 mm, 4 mm, 5 mm, 6 mm, 7 mm, 8 mm or 9 mm thick.

Advantageously, the use of one or more flexible materials in the manufacture of the crown portion allows the crown portion to better conform to the temperature control probe during heat transfer in some instances, in use. This is beneficial, for example, in ensuring a good contact is maintained between the crown portion and the temperature control probe such that heat can be effectively conducted from the temperature control probe to the crown portion, and heat loss from the temperature control probe to, for example, surrounding air, can be correspondingly minimized. The use of a collapsible crown is also beneficial as it enables the use of more economical materials which can be used as disposable components.

Preferably, the crown portion is made of one or more rigid materials such that the crown portion is rigid. Preferably the rigid material is between about 0.2 and 10 mm thick. In some embodiments it may be about 1, 2, 3, 4, 5, 6, 7, 8 or 9 mm thick.

Advantageously, the use of one or more rigid materials in the manufacture of the crown portion allows the crown portion to better contact the temperature control probe during heat transfer in some instances, in use. This is beneficial, for example, in ensuring a good contact is maintained between the crown portion and the temperature control probe such that heat can be effectively conducted from the temperature control probe to the crown portion, and heat loss from the temperature control probe to, for example, surrounding air, can be correspondingly minimized. The use of a rigid crown portion is also beneficial as the component is robust and can be cleaned and reused on numerous occasions.

Preferably, the crown is made of one or more materials that are able to create a seal.

Advantageously, the closure is able to seal the liquid in the container or includes a discrete seal itself attached thereto. Preferably, the one or more sealing and/or crown materials are food grade.

Advantageously, the one or more food grade materials further prevent contamination of the liquid in the container.

Advantageously, the crown allows the liquid in the container to be heated without the need for prior removal of the crown, and insertion of, for example, a temperature control probe into the container. This inhibits the liquid in the container from becoming contaminated due to, for example, contact with the temperature control probe. This is further beneficial in affording user convenience since the crown does not need to be removed, for example, until the liquid in the container is heated and ready to be used.

Advantageously, the substantially whole and direct contact between the outer surface area of the crown and the liquid improves the efficiency of heat transfer from the closure to the liquid.

Preferably, the engagement portion sealingly abuts a rim of the container by adhesion by an adhesive.

Preferably, the engagement portion is removable from the rim by peeling.

Advantageously, the closure is easily and conveniently removable from the rim.

Preferably, the container is adapted to removably receive the overcap which may include a compression ring, and wherein the engagement portion of the closure sealingly abuts the rim of the container by being compressed between the compression ring and the rim when the cap is located on the container.

Preferably, the crown portion further comprises a weakened portion such that the liquid sealed in the container may be accessed in a controlled manner when the weakened portion is punctured.

Advantageously, the crown portion can be easily punctured such that a liquid retrieval device, for example, a straw can be used to access the liquid in the container.

Preferably, the crown portion is made of one or more substantially rigid materials such that the crown portion is substantially rigid.

Advantageously, the use of one or more substantially rigid materials in the manufacture of the crown portion a lower mating force between the temperature control probe and the crown portion since an invagination may be already formed into the crown portion This is also beneficial, for example, in ensuring a good contact is maintained between the crown and the temperature control probe such that heat can be effectively conducted from the temperature control probe to the crown, and heat loss from the temperature control probe to, for example, surrounding air, can be correspondingly minimized. The use of a substantially rigid crown is also beneficial as the component is robust and can be cleaned and reused on numerous occasions. Preferably the crown is manufactured from stainless steel, a polymer, a steel, an alloy, aluminium, ceramic, or the like.

Preferably, the container comprises a wall defining the opening of the container, the wall having a rim region disposed adjacent to the rim and the engagement portion comprises a skirt portion that extends beyond the rim to cover the rim region.

Advantageously, the skirt portion of the closure covers the rim region until the crown and engagement region is removed. This can be beneficial, for example, when the liquid in the container is to be consumed directly from the container after heating. In such instances, the rim region, which comes into contact with a user's mouth, is covered with the skirt portion and prevented from being contaminated during, for example, storage and transport of the liquid.

According to another aspect of the present invention there is provided a container for holding liquid, the container defining an inner region inside which liquid is adapted to be held, the container including one or more walls for facilitating heating or cooling of the liquid therethrough, the one or more walls being adapted for invagination by a temperature control probe such that the temperature control probe extends into the container without directly contacting contents of the inner region of the container.

Preferably the one or more walls include a window of a discrete window material adapted for invagination by the temperature control probe. The material may be a resilient membrane or a substantially rigid material formed into a closed hole substantially corresponding in shape to the heating or cooling probe.

Preferably the window is an aperture which is closed in use by a closure as herein described. Preferably the container is adapted to contain milk. Preferably the container is adapted to contain blood. The crown portion may be a window panel such that the window and window panel may not be disposed at a top portion of a closure or wall, but on a side or a bottom of a wall.

According to yet another aspect of the present invention there is provided an apparatus for controlling temperature of liquid within a container, the apparatus comprising:
one or more temperature control probes;
a temperature controller operatively connected to the one or more temperature control probes, the temperature controller adapted for controlling temperature in the one or more temperature control probes wherein the one or more temperature control probes are adapted to invaginate or be otherwise inserted into a wall, or window, crown or other panel of a closure as hereindescribed or a container as hereindescribed for heat transfer through the wall or window or crown.

Advantageously, the temperature control apparatus allows the liquid in the container to be heated by heat transfer from the temperature control probe to the inner surface area of the crown of the closure, without the need for prior removal of the closure, and insertion of, for example, a temperature control probe into the container. This inhibits the liquid in the container from becoming contaminated due to, for example, contact with the temperature control probe.

Advantageously, the amount of heat being transferred to the liquid in use is a specified amount of heat energy generated by the temperature control probe, and the specified amount of energy is provided by a power source, respectively.

Preferably, the temperature control probe is geometrically complementary to the crown such that the temperature control probe is substantially wholly in contact with the outer surface area of the crown during heat transfer.

Advantageously, the substantially whole contact between the temperature control probe with the crown, in use, facilitates that as much of the heat generated as possible is substantially transferred to the outer surface of the crown and correspondingly, the amount of heat loss from the temperature control probe to, for example, surrounding air is minimised.

Advantageously, the substantially maximum contact of the temperature control probe with the inner surface of the crown, in use, also ensures that a maximum surface area of the temperature control probe and the inner surface of the crown are used to effect heat transfer via conduction from the temperature control probe to the crown.

Preferably the apparatus includes a dock which is adapted to receive a container as above described. The dock may include a dock base and one or more temperature control probes disposed thereon which extend upwardly from the dock base. Preferably in use the dock receives the container such that the container is inverted for temperature control of a liquid inside the container.

Preferably a temperature sensor is provided to sense an initial temperature of a liquid in the container prior to control of the temperature of the liquid. Preferably the temperature sensor is selected from the group consisting of a thermocouple, a thermistor, an infrared thermometer, and a solid state temperature sensor.

Preferably a user input terminal is provided to receive user inputs including those selected from the group consisting of final desired temperature of the liquid, a specific heat capacity of the liquid, a mass of the liquid in the container, and a maximum permissible liquid temperature.

Preferably the apparatus includes a processor which is adapted to calculate output energy based on user inputs to the user input terminal.

Preferably the apparatus includes a mass sensor to sense the mass of the liquid in the container.

Preferably the apparatus includes a power source, which may be portable and in the form of a battery, for example.

Preferably, the container is located above the temperature control probe in use.

Advantageously, the liquid is correspondingly located above the crown and the temperature control probe during heat transfer. This facilitates the liquid making contact with the crown portion even when the container is not completely filled with the liquid. Additionally, having the liquid located above the temperature control probe enables more convection within the liquid than, for example, having the liquid located below the temperature control probe during heat transfer. Convection increases the rate of heat transfer from the crown to the liquid, and further inhibits inadvertent overheating of the liquid in contact with the inner surface area of the crown during heat transfer.

Advantageously, the initial temperature of the liquid may be determined without the need for removal of the closure, and insertion of, for example, an external temperature measurement device such as a thermometer into the container. This inhibits the liquid in the container from becoming contaminated due to, for example, contact with the external temperature measurement device.

Advantageously, the temperature control apparatus is compatible for use with a range of different types and volumes of liquids since the apparatus contains one or more pre-programmed inputs that define the type or volume of the liquid in the container.

Advantageously, the processor can be set to not heat the liquid above a preset maximum temperature so that the integrity of a heat-sensitive liquid can be maintained. This is beneficial in a case where, for example, the liquid is milk and wherein the substantial amounts of proteins or other nutrients contained in the milk may be denatured when the liquid is exposed to high temperatures for a period of time. This is particularly relevant where the second surface area of the crown is not fully immersed in the milk when the container is substantially inverted on the temperature control apparatus during heating, as a temperature greater than the preset maximum temperature may cause damage to the proteins or other nutrients of milk particularly at the interface between the milk, the air in the container and the inner surface area of the crown.

Advantageously, the temperature control apparatus is compatible for use with a range of different types and volumes of liquids since the user is able to input the one or more inputs that define the type or volume of the liquid in the container at the user input terminal.

Advantageously, a heat loss correction factor allows the processor to vary the heat energy input to the temperature control probe to take into consideration external factors such as heat loss to the surrounding from, for example, the temperature control probe and the container. Furthermore, the heat loss correction factor allows the processor to take into consideration system factors such as heat generation efficiency of, for example, the temperature control probe, and energy transfer efficiency of, for example, the power source to the temperature control probe.

Preferably, the temperature control apparatus further comprises a mass measure located to measure the mass of the liquid in the container prior to heating.

Advantageously, the mass measure allows the mass of the liquid to be measured prior to heating such that the measured mass of the liquid can form, for example, a pre-programmed input corresponding to the mass of the liquid in the container, or be displayed on a display screen or other display device such that a user can input the mass of the liquid into the input user terminal.

In accordance with yet another aspect of the present invention there is provided a method of controlling temperature of a liquid in a container adapted to receive a temperature control probe, the method including the steps of:

providing a temperature control probe to the container via an invagination in a wall of the container; and generating the amount of energy required in the temperature control probe to raise the temperature of the liquid to the desired temperature.

Preferably the method further includes the following steps:

measuring an initial temperature of liquid in the container; obtaining one or more of the following data:
   i. the final desired temperature of the liquid in the container;
   ii. a specific heat capacity of the liquid in the container;
   iii. a mass of the liquid in the container;
   iv. a heat loss correction factor; and
calculating an amount of energy required to heat or cool the liquid to the desired temperature as a function of the initial temperature and the data.

Preferably the method further includes the steps of calculating heat required to heat a container of fluid based on one or more of: the desired temperature of the liquid, specific heat capacity of the liquid, mass of the liquid, and heat loss correction factor. The kind of control of these preferred embodiments is feed forward control. Advantageously, this feed forward control is an efficient way of delivering heat energy to a fluid since power spikes are reduced and the control is more even and stable, which is particularly advantageous when battery power is utilised.

In another aspect, the present invention provides use of a temperature control probe to alter the temperature of a liquid in a container adapted to receive a temperature control probe, wherein the temperature control probe is isolated from direct contact with the liquid in the container by a wall.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form component of the prior art base or were common general knowledge in the field relevant to the present invention as it existed in Australia prior to development of the present invention.

In order that the present invention may be more clearly understood, preferred embodiments will be described with reference to the following drawings and examples.

BRIEF DESCRIPTION OF THE DRAWINGS

In order to enable a clearer understanding of the present invention, preferred embodiments of the invention will now be described, by way of example only, with reference to the accompanying drawings in which.

DETAILED DESCRIPTION OF SPECIFIC EMBODIMENTS

Figure 1:
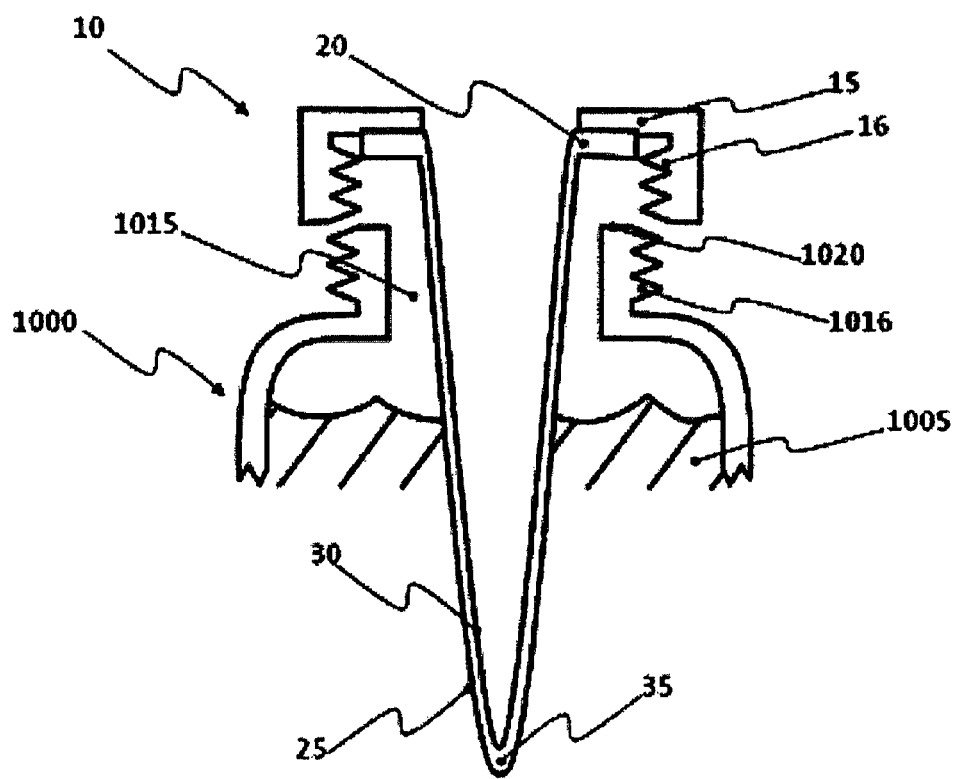
FIG. 1 is a partial sectional side elevation view of a closure suitable for sealing and transferring heat to a liquid in a container, the closure comprising an engagement arrangement to engage a complementary engagement portion of the container, and a crown portion in accordance with a preferred embodiment of the present invention.

It should be noted in the following description that like or the same reference numerals in different embodiments denote the same or similar features.

Referring to FIG. 1, in accordance with one embodiment of the present invention, a closure 10 for transferring heat to a liquid 1005 in a container 1000 in use is provided. In this embodiment, the container 1000 is a baby bottle suitable for holding baby feed such as milk, that is suitable for heating to, for example, a body temperature of approximately 37° C., before being fed to a baby. In other embodiments, however, the container 1000 may be arranged for other purposes and/or to hold other liquids such as for example blood, which is held in flexible-walled bags. In the embodiment shown in FIG. 1, the closure 10 comprises an overcap 15 having an engagement arrangement 16 to engage a cooperative engagement arrangement 1016 of the container 1000 immediately adjacent to an opening 1015 of the container 1000 such that the liquid 1005 is sealed in the container 1000. In a preferred embodiment, the engagement arrangement 16 is a threaded arrangement and the cooperative engagement arrangement 1016 is a complementary thread adapted to receive the threaded arrangement. In another embodiment, the engagement arrangement 16 is a smooth surface and the cooperative engagement 1016 is a complementary smooth and flexible surface, such as one made of an elastomer, adapted to form a press fit with the smooth surface of the engagement arrangement 16. It will therefore be appreciated that the engagement arrangement 16 and the cooperative engagement arrangement 1016 may take any suitable form within the scope of the present invention.

Figure 2:
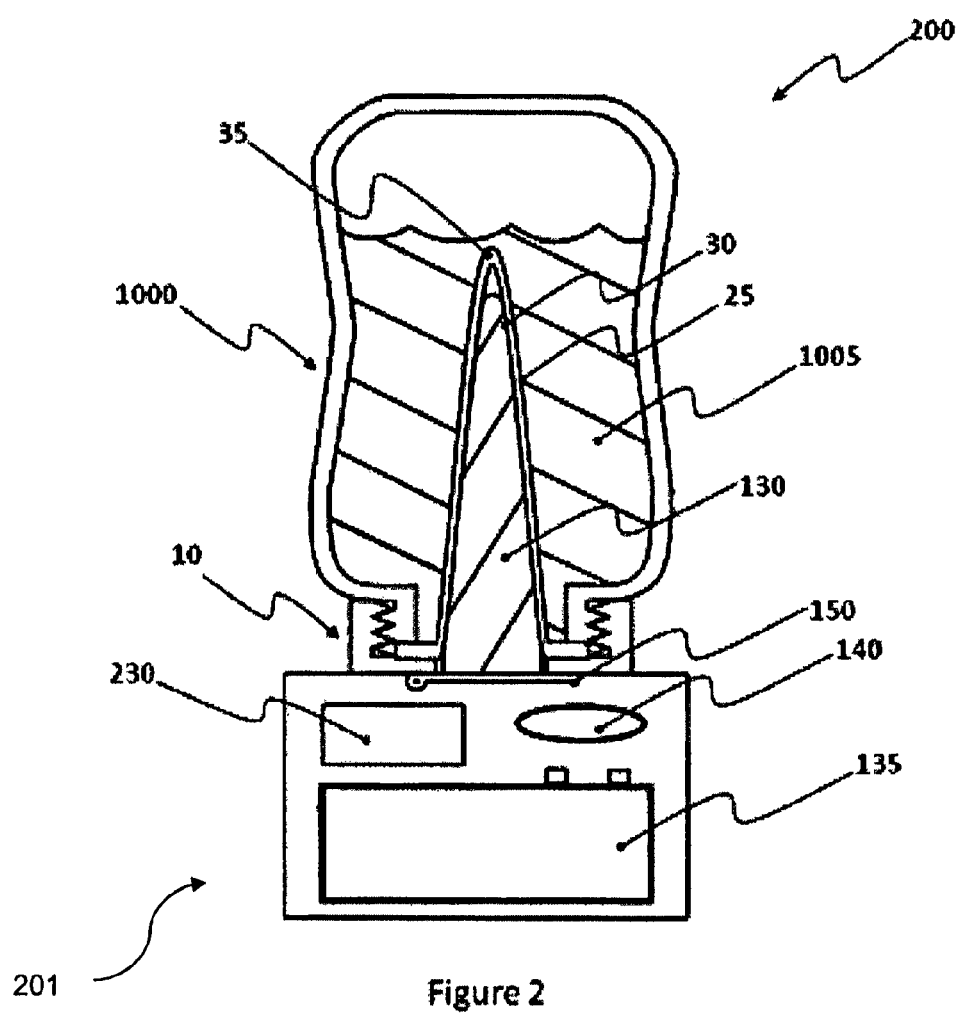
FIG. 2 is a sectional side elevation view of the closure and container of FIG. 1, the container being substantially inverted and located on a dock of a temperature control apparatus, the apparatus comprising a temperature control probe, a power source for powering the temperature control probe, and a user input terminal, such that in use an outer surface of the crown portion of the closure is substantially wholly in contact with the temperature control probe, in accordance with another preferred embodiment of the present invention.

In this embodiment, the closure 10 further comprises a crown portion 20 being heat conductive and having a total heat transfer surface area including a outer surface 30 and a second surface area 25 such that, in use, the outer surface 30 contacts a temperature control probe 130 as shown in FIG. 2, and the second surface area 25 contacts the liquid 1005 to allow heat to be transferred from the temperature control probe 130 to the liquid 1005. The crown portion 20 may be a panel or other surface which extends between edge regions of the engagement region to cover the opening of the container.

In one embodiment, the crown portion 20 and the overcap 15 are constructed as a single part. In another embodiment, the crown portion 20 and the overcap 15 are constructed as separate parts and the crown portion 20 is removably connected to the overcap 15. In this embodiment, the crown portion 20 is held between the overcap 15 and a rim 1020 of the container 1000 when the engagement arrangement 16 of the overcap 15 is engaged to the cooperative engagement arrangement 1016 of the container 1000 as shown in FIG. 2. Alternatively, the crown portion 20 can be removably connected to the overcap 15 by means of, for example, a screw threaded arrangement, before the overcap 15 is engaged to the container 1000. It will be appreciated, therefore, that any suitable means of connecting the crown portion 20 to the overcap 15 is possible within the scope of the present invention including adhesive.

Referring once again to FIG. 1, in a preferred embodiment, the crown portion 20 comprises one or more projections 35 that function to increase the total heat transfer surface area. In one embodiment, the one or more projections 35 are a major single projection with a large surface area to volume ratio, for example, a tetrahedron or a cube. In another embodiment, the one or more projections 35 are numerous projections of a suitable packing geometry, such as rectangular cuboid, that have a large total surface area to total volume ratio when considered together. It will therefore be appreciated that any suitable combination of the number and geometry of the one or more projections 35 to increase the total heat transfer surface area, and maximise the total surface area to total volume ratio of the one or more projections 35 is possible within the scope of the present invention. In this embodiment, and as shown in FIG. 1, the crown portion 20 comprises one projection 35 which is substantially conical in shape. In the embodiment shown, in FIG. 1, the projection 35 is either adapted to be forced into by an external probe, or pre-formed into, a recess or invagination so as to extend into the container to facilitate contact with a large volume of fluid in the container for better heat transfer by conduction to the crown 20. There may be minor projections, not shown, of heat transfer fins or villi to further improve the contact between the crown 20 and the fluid.

In a preferred embodiment, the closure 10 is made from one or more materials selected from a polymer, a ceramic, a glass, a substantially non-corroding metal, or a combination thereof. In this embodiment, the crown portion 20 of the closure 10 is made from one or more materials with good thermal conductivity such as stainless steel and the overcap 15 of the closure 10 is made from one or more materials with good temperature resistance, and good sealing properties, such as certain engineering polymers. Furthermore, the one or more materials used in the manufacture of the closure 10 are food grade materials. It will be appreciated that the material of the crown portion 20 is not limited to stainless steel, but that other materials, including but not limited to: copper, aluminium, other alloys, ceramic, may also be used. In a preferred embodiment, the crown 20 is made from stainless steel, such as austenitic steel, as it is a food grade material. The temperature control probe 130 is also preferably manufactured from a material with good thermal conductivity.

In one embodiment, the crown portion 20 is made of one or more flexible materials such that the crown portion 20 is collapsible. The use of a collapsible crown portion 20 is beneficial as it enables the use of more economical materials which can be used as disposable components. In another embodiment, the crown portion 20 is made of one or more rigid materials such that the crown portion 20 is rigid. The use of a rigid crown portion 20 is also beneficial as it is robust and can be cleaned and reused on numerous occasions.

Figure 3:
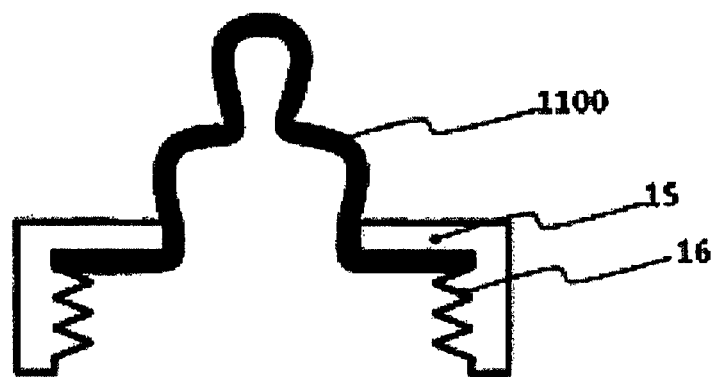
FIG. 3 is a sectional side elevation view of the closure of FIG. 1, wherein the crown portion has been replaced with a teat, in accordance with another preferred embodiment of the present invention.

Referring to FIGS. 1 and 3, in this embodiment, the overcap 15 of the closure 10 is also adapted to receive a teat 1100 when the crown portion 20 is removed. It is contemplated that the crown portion 20 may be in the form of a teat which may be pushed inwards and stretched to form an invagination or recess so as to heat the fluid in the way expressed by preferred embodiments of the present invention. In this manner, a separate teat is not required. In this embodiment the teat may be pierced adjacent or through a weakened portion in the teat so as to access the liquid in the container. Then the teat may be withdrawn from the container to form a teat again for dispensing from the bottle or container.

In other embodiments, wherein the crown portion 20 is, for example, not removable from the overcap 15, the cooperative engagement arrangement 1016 of the container 1000 may further receive one or more additional parts (not shown) adapted for use with the container 1000 to enable the teat 1100 to be located on the container 1000. For example, the one or more additional parts may include the teat 1100 arranged on a teat holder (not shown) adapted to cooperatively engage with the container 1000 using the cooperative engagement arrangement 1016 of the container 1000. Accordingly, in this respect, the cooperative engagement arrangement 1016 can be used for coupling both the teat holder and the closure 10 to the container 1000.

Referring once again to FIGS. 1 and 2, the closure 10 functions both as a heat transfer device that enables heat to be transferred from the temperature control probe 130 to the liquid 1005 in the container 1000, and as a cap for sealing the liquid 1005 in the container 1000 for purposes other than heat transfer, such as storage or transport of the liquid 1005. Sealing the liquid 1005 in the container 1000 further inhibits, for example, spillage of the liquid 1000 during heat transfer. As a result of the liquid 1005 being sealed, it is possible, in this embodiment, to substantially orient the container 1000 such that the closure 10 is located below the container 1000, and correspondingly, the liquid 1005 is located above the closure 10 in use. This ensures that the liquid 1005 makes maximum contact with the crown portion 20 of the closure 10 even when the container 1000 is not completely filled with the liquid 1005. Additionally, having the liquid 1005 located above the closure 10 enables more convection within the liquid 1005 than, for example, having the liquid 1005 located below the closure 10 during heat transfer, in use.

Convection increases the rate of heat transfer from the closure 10 to the liquid 1005, and further inhibits inadvertent overheating of the liquid 1005 in contact with the second surface area 25 of the crown portion 20 during heat transfer. In this embodiment, the one or more projections 35 are preferably of a suitable size such that the second surface area 25 of the one or more projections 35 is in full contact with the liquid 1005 when the container 1000 is not completely filled with the liquid 1005. It will be appreciated, therefore, that in such instances, a range of closures 10 with one or more suitably sized projections 35 for transferring heat could be manufactured to cater for a range of volumes of liquid 1005.

In this embodiment, the crown 20 of the closure 10 allows the closure 10 to function as a heat transfer device such that heat may be transferred from the temperature control probe 130 to the liquid 1005 in the container 1000 without the need for prior removal of the closure 10, and insertion of, for example, an external heat transfer device into the container 1000. Therefore, a primary function of the crown portion 20 is to transfer heat efficiently and promptly from the temperature control probe 130 to the liquid 1005 in the container 1000. Concomitantly, in this embodiment, the overcap 15 allows the closure 10 to function as a cap for sealing the liquid 1005 in the container 1000. Therefore, a primary function of the overcap 15 is to ensure that a good seal is formed, for example, between the crown 20 and the rim 1020 of the container 1000 or between the overcap 15 and the rim of the rim 1020 of the container 1000 by virtue of the cooperative engagement arrangement 1016 of the container 1000 such that the liquid 1005 is sealed in the container 1000. Further, a secondary function of the overcap 15 is to act as a heat insulator to provide a user a cool grip on the closure 10 such that the closure 10 may be easily removed from the container 1000 immediately after heat transfer. As such, preferably, the crown portion 20 and the overcap 15 are made of different materials according to their respective functions. In this embodiment, the crown portion 20 is made of one or more materials with good thermal conductivity such that the crown portion 20 may transfer heat efficiently and promptly; and the overcap 15 is made of one or more materials with good temperature resistance, and that are able to create a seal, such that the overcap 15 may be cool to the touch immediately after heat transfer, and further effectively seal the liquid 1005 in the container 1000, respectively. In this embodiment, the crown portion 20 is removably connected to the circumferential portion 15 such that the crown portion 20 and the overcap 15 can be conveniently made from different materials.

In this embodiment, the crown portion 20 can be removed from the overcap 15 such that the crown portion 20 and the overcap 15 can be subjected to separate treatments (for instance, sterilization), or can be disposed of independently. For example, it may be necessary for the crown portion 20 to be subjected to a more stringent sterilization process (for instance, higher temperatures) than the overcap 15, since the crown portion 20 comes into direct contact with the liquid 1005 in use. In a further example, it may be desirable for the crown portion 20 that is made of, for example, stainless steel, to be reusable over a relatively long period of time due to the relatively high cost of the one or more materials used during its manufacture. Conversely, it may not be as critical for the overcap 15 that is made of, for example, an engineering polymer or wood to be as long lasting compared to the crown portion 20 due to the relatively low cost of the one or more materials used during its manufacture. As such, the overcap 15 may be replaced independently once, for example, the sealing property of the overcap 15 has deteriorated due to conditions such as wear and tear in use.

In this embodiment, the closure 10 and the container 1000 can be subject to separate treatments (for instance, sterilization), or can be disposed of independently. In one embodiment, the liquid 1005 is packaged for sale in the container 1000 and supplied with the closure 10 such that both the closure 10 and the container 1000 may be disposed of after a single use. In this embodiment, the closure 10 further comprises a tamper evident portion (not shown) adapted to, for example, tear from the closure 10 when the closure 10 is initially disengaged from the container 1000. This allows the tamper evident portion to provide a guarantee for the integrity of the liquid 1005 in the container 1000.

In another embodiment, the closure 10 is reusable and supplied for use on a disposable container 1000. For example, the liquid 1005 can be packaged for sale in the container 1000 with a storage cap (not shown) or any other suitable sealing means. When the liquid 1005 is ready to be heated for use, the storage cap is replaced with the closure 10 such that heat can be transferred to the liquid 1005 in the container 1000. After use, the container 1000 and the storage cap can be disposed of while the closure 10 is sterilized for further use.

In this embodiment, the one or more projections 35 function to increase the total heat transfer surface area, and to correspondingly increase the rate of heat transfer from the temperature control probe 130 to the liquid 1005. The projections 35 also function to receive a temperature probe 130 shown in FIGS. 2, 6, 7 and 8 in a recess or invagination which cooperates with the shape of the temperature probe 130, either by being flexible and resilient enough to take the form of the temperature probe 130 or by being pre-formed into a shape cooperating with the temperature probe 130. Also, the increased surface area to volume ratio of the shape formed by the one or more projections 35 further increases the rate of heat transfer from the temperature control probe 130 to the liquid 1005. The large total heat transfer surface area is particularly significant, for example, in instances when the liquid 1005 to be heated is heat sensitive, and should not be subject to a large temperature gradient to increase the rate of heat transfer during the heat transfer process. An example of such a liquid 1005 is milk, wherein the proteins or other nutrients contained in the milk may be denatured when the liquid 1005 is exposed to high temperatures for a period of time such as that in excess of approximately 60° C. to 70° C. In these instances, the increased total heat transfer surface area aids in minimising the time taken for the liquid 1005 to be heated, other things being equal.

In this embodiment, the use of non-corroding and food grade materials in the manufacture of the closure 10 inhibits contamination of the liquid 1005 in the container 1000 in use. In one embodiment, the use of one or more flexible materials in the manufacture of the crown portion 20 allows the crown portion 20 to better conform to the temperature control probe 130 during heat transfer, in use. This is beneficial, for example, in ensuring a good contact is maintained between the crown portion 20 and the temperature control probe 130 such that heat can be effectively conducted from the temperature control probe 130 to the crown portion 20, and heat loss from the temperature control probe 130 to, for example, surrounding air, can be correspondingly minimized. In another embodiment, the use of one or more rigid materials in the manufacture of the crown portion 20 allows the crown portion 20 to better contact the temperature control probe 130. It will be appreciated, therefore, that any suitable type of material may be used to ensure that a good contact is achieved between the crown portion 20 and the temperature control probe 130.

Referring once again to FIG. 2, according to a second embodiment of the present invention, a temperature control apparatus 200 for heating a liquid 1005 from an initial temperature to a final desired temperature is provided, comprising a container 1000 for containing the liquid 1005, having a closure 10 as described in the first embodiment of the present invention; a temperature control apparatus 200 comprising a temperature control probe 130; and a power source 135 for powering the temperature control probe 130 such that the temperature control probe 130 generates and transfers a specified amount of heat energy to the outer surface 30 of the crown portion 20 of the closure 10 in response, and corresponding to, a specified amount of energy provided by the power source 135, such that the liquid 1005 is heated via the second surface area 25 of the crown portion 20.

In this embodiment, the temperature control probe 130 is geometrically complementary to the crown portion 20 such that the temperature control probe 130 is substantially in full and direct contact with the outer surface 30 of the crown portion 20 during heat transfer in use. For example, wherein the crown portion 20 of the closure 10 comprises a single projection 35 of substantially conical geometry, as shown in FIG. 2, the temperature control probe 130 is complementarily conical such that the temperature control probe 130 is substantially in full and direct contact with the outer surface 30 of the crown portion 20 during heat transfer, in use. In a further example, wherein the crown portion 20 of the closure 10 comprises multiple projections (not shown) of rectangular cuboid geometry, the temperature control probe 130 comprises projections that are complementary in number and geometry such that the temperature control probe 130 is substantially in full and direct contact with the outer surface 30 of the crown portion 20 during heat transfer in use. It will therefore be appreciated that the temperature control probe 130 may be of any suitable geometry that affords the temperature control probe 130 a substantially full and direct contact with the internal surface area 30 of the crown portion 20 during heat transfer in use.

In this embodiment, the temperature control probe 130 is manufactured from one or more electrically resistive materials that generate heat when conducting electrical current. Preferably, the one or more electrically resistive materials have positive temperature coefficients such that the one or more electrically resistive materials are able to prevent the temperature of the temperature control probe 130 from increasing above a preset maximum temperature. In this respect, the temperature control apparatus 200 can be made safe for use since the temperature of the temperature control probe 130, and ultimately the second surface area 25 in contact with the liquid 1005, will not exceed the maximum temperature, in use. This is particularly beneficial in making the temperature control apparatus 200 suitable for use with heat sensitive liquids 1005. For example, wherein the liquid 1005 to be heated is milk, and wherein the substantial amounts of proteins or other nutrients contained in the milk may be denatured if exposed to high temperatures for a period of time, such as temperatures in excess of approximately 60° C. to 70° C., the maximum temperature can be set so that the temperature of the second surface area 25 will not exceed the maximum temperature which will cause the milk proteins and nutrients to denature. In a further example, wherein the liquid 1005 to be heated is blood, the maximum temperature can be set so as to prevent undesirable heat-induced cell destruction (e.g. haemolysis) if the temperature of the second surface area 25 becomes too great. In this instance, preferably, the maximum temperature is set so that the temperature of the second surface area 25 will not exceed the maximum temperature range of 37° C. to 50° C.

The ability to set the maximum temperature will be beneficial in circumstances where the second surface area 25 of the crown portion 20 is not fully immersed in the liquid 1005 when the container 1000 is substantially inverted on the temperature control apparatus 201 during heating. In this instance, the second surface area 25 being partially exposed to the air in the container 1000 may heat up more quickly than the part of the second surface area 25 immersed in the liquid 1005, and as there is likely to be an uneven heat dissipation along the second surface area 25, the part of the second surface area 25 partially exposed to air may reach a temperature that is greater than a desired temperature needed for heating the liquid 1005. As such, if the liquid 1005 then contacts the exposed part of the second surface area 25, particularly for a prolonged period of time, then there is a chance that if the liquid 1005 is a heat-sensitive liquid 1005 such as milk, a temperature greater than the desired temperature for heating the milk may cause damage to the proteins or other nutrients in the milk, particularly at the interface between the milk, the air in the container 1000 and the second surface area 25 of the crown portion 20.

In an alternative embodiment, the power source 135 may be adapted to only deliver a certain amount of energy to the temperature control probe 130 such that the maximum temperature of the temperature control probe 130 is limited to the preset maximum temperature.

In this embodiment, the liquid 1005 is first sealed in the container 1000 by the overcap 15 of the closure 10, and then the container 1000 is substantially inverted such that the container 1000 is located above the temperature control probe 130 and correspondingly, the liquid 1005 is located above the closure 10 and the temperature control probe 130 during heat transfer, in use. This ensures that the liquid 1005 makes contact with the closure 10 even when the container 1000 is not completely filled with the liquid 1005. Additionally, having the liquid 1005 located above the temperature control probe 130 enables more convection within the liquid 1005 than, for example, having the liquid 1005 located below the temperature control probe 130 during heat transfer, in use. Convection increases the rate of heat transfer from the closure 10 to the liquid 1005, and further inhibits inadvertent overheating of the liquid 1005 in contact with the second surface area 25 of the crown portion 20 during heat transfer. It will be appreciated, however, that in the preferred embodiment the container 1000 may be substantially oriented in any suitable position with respect to the temperature control probe 130 so long as the entirety of the second surface area 25 of the crown portion 20 of the closure 10 is in contact with, and fully immersed in, the liquid 1005 in use.

In this embodiment, the temperature control apparatus 200 further comprises a temperature sensor (not shown) located to measure approximately the initial temperature of the liquid 1005 prior to heat transfer. In one embodiment, the temperature sensor is located such that the temperature sensor can be used to determine the temperature of the liquid 1005 in the container 1000 through the container 1000. In another embodiment, the temperature sensor is located such that the temperature sensor can be used to determine the temperature of the liquid 1005 in the container 1000 through the crown portion 20 of the closure 10. It will therefore be appreciated that the temperature sensor may be located anywhere on the temperature control apparatus 200 to enable convenient approximation of the initial temperature of the liquid 1005 in the container 1000 without needing to remove the closure 10. Preferably, the temperature sensor is selected from any one of the following types of temperature sensor:
  i. a thermocouple;
  ii. a thermistor;
  iii. an infrared thermometer; and/or
  iv. a solid state temperature sensor.

The temperature sensors and other measuring devices may be disposed on the probe 130.

For example, a thermocouple, possibly disposed on the probe 130 can be used to determine approximately the initial temperature of the liquid 1005 in the container 1000 by measuring the temperature of the crown portion 20 of the closure 10. It will be appreciated, however, that the type of temperature sensor is not limited to those described above and that any other suitable temperature sensor may be used to determine approximately the initial temperature of the liquid 1005 in the container 1000.

In this embodiment, the temperature control apparatus 200 further comprises an input bank (not shown) adapted to contain one or more pre-programmed inputs. Preferably, the one or more pre-programmed inputs include one or more of the following:
  i. an input corresponding to the final desired temperature of the liquid;
  ii. an input corresponding to a specific heat capacity of the liquid;
  iii. an input corresponding to a mass of the liquid in the container 1000; and
  iv. an input corresponding to a maximum temperature of the liquid 1005.

In this respect, by having a pre-programmed input for the maximum temperature described above, the temperature of the temperature control probe 130, and ultimately the second surface area 25 in contact with the liquid 1005, will not exceed the maximum temperature, in use, such that the integrity of the heat-sensitive liquid 1005 can be maintained.

In this embodiment, the temperature control apparatus 200 further comprises a user input terminal 140 adapted to receive one or more inputs from the user. In a preferred embodiment, the one or more inputs take the form of one or more pre-programmed buttons corresponding to the type of liquid 1005 (for instance, milk or soup) to be heated. In another embodiment, the one or more inputs may take the form of one or more numerical values corresponding to properties of the liquid 1005 (for instance, temperature, mass or specific heat capacity). It can be appreciated, however, that the one or more inputs may take any suitable form within the scope of the present invention. Preferably, the one or more inputs include one or more of the following:
  i. an input corresponding to the initial temperature of the liquid;
  ii. an input corresponding to the final desired temperature of the liquid;

iii. an input corresponding to the specific heat capacity of the liquid; and iv. an input corresponding to the mass of the liquid in the container.

In a preferred embodiment, the temperature control apparatus 200 further comprises a mass measure 150 adapted to determine the mass of the liquid 1005 in the container 1000. In this embodiment, the mass measure 150 is located below the temperature control probe 130 such that the mass measure 150 may be used to determine the mass of the liquid 1005 in the container 1000 when the container 1000 containing the liquid 1005 and engaged with the closure 10 is located on the temperature control probe 130, as shown in FIG. 2. In this embodiment, the mass measure 150 is adapted to give a reading of zero when an empty container 1000 with the closure 10 is placed on the temperature control probe 130 such that the mass measure 150 measures only the mass of the liquid 1005. In another embodiment, the temperature control apparatus 200 comprises a zero button (not shown) that allows the user to give the mass measure 150 the reading of zero when the zero button is depressed. In this embodiment, the mass measure 150 comprises a strain gauge based load cell (not shown).

In an alternative embodiment, the temperature control apparatus 200 may further comprise a display screen (not shown) to display the mass of the liquid 1005 once it has been measured using the mass measure 150. For example, the display screen could be an LCD display screen operatively connected to the mass measure 150 and powered by the power source 135. It will be appreciated that in this embodiment, the LCD display screen could also be operatively connected to the temperature sensor to display the temperature of the liquid 1005. In this embodiment, the user can obtain both the initial temperature and mass of the liquid 1005 from the LCD display and input these values into the user input terminal 140.

In another alternative embodiment, the container 1000 may comprise a graduated scale (not shown) located on the side of the container 1000 such that when the container 1000 containing the liquid 1005 is sealed by the overcap 15 of the closure 10, and then substantially inverted on the temperature control apparatus 200, the level of the liquid 1005 can be measured using the graduated scale to provide the volume of liquid 1005. Knowing the density of the liquid 1005 will therefore enable the mass of the liquid 1005 to be calculated.

In another embodiment, the mass measure 150 could be a liquid level sensor (not shown) to measure the volume of the liquid 1005, which can then be used to calculate the mass of the liquid 1005 if the density of the liquid 1005 is known. The liquid level sensor could be any type of sensor used in the measurement of liquid levels, including, but not limited to any one of the following: an ultrasonic level sensor, an optical level sensor (e.g. laser light or light emitting diode), a sight glass, a float level sensor, a hydrostatic pressure level sensor, a capacitance level sensor. It can be appreciated, however, that a preferred liquid level sensor will be one which has little or no contact with the liquid 1005, such as an ultrasonic or an optical level sensor.

It will be appreciated, however, that any other types of load cells within the scope of the present invention may be used in the mass measure 150.

Preferably, the temperature control apparatus 200 further comprises a processor 230 adapted to calculate an output value corresponding to the specified amount of power as a function of one or more of the following:

i. the initial temperature of the liquid;

ii. the final desired temperature of the liquid;

iii. the specific heat capacity of the liquid;

iv. the mass of the liquid in the container; and v. a heat loss correction factor.

It will be appreciated that the processor may be any suitable kind of processing system such as for example a suitably programmed PC, terminal, laptop, handheld PC or the like. The processor may be connected to a memory, an input-output device and a visual display output such as a screen or LCD or LED output, and an external interface all coupled together via a bus. The external interface may be connected to an external communications network via a network interface card and a wired port or a wireless protocol such as for example Bluetooth.

Preferably, the power source 135 is a battery, a power supply connected to mains electricity or an exothermic reaction, in use. The power source may be a battery charged by a wind-up mechanism or other similar kind of mechanical charger. In this embodiment, the power source 135 is a battery. In other embodiments, the temperature control apparatus 200 may further comprise one or more adaptors that allow the temperature control apparatus 200 to receive one or more corresponding types of power source 135 according to the circumstances of the user. In yet other embodiments, the temperature control apparatus 200 may further comprise connectors adapted to allow a rechargeable battery to be recharged by, for example connected to mains electricity.

In this embodiment, the temperature control apparatus 200 allows the liquid 1005 in the container 1000 to be heated by heat transfer from the temperature control probe 130 to the outer surface 30 of the crown portion 20 of the closure 10, without the need for prior removal of the closure 10, and insertion of, for example, an external heat transfer device into the container 1000.

In this embodiment, the full and direct contact of the temperature control probe 130 with the outer surface 30 of the crown portion 20, in use, ensures that most of the specified amount of heat generated is substantially transferred to the liquid 1005 via the crown portion 20, and correspondingly, the amount of heat loss from the temperature control probe 130 to, for example, surrounding air is minimized. Furthermore, the full and direct contact also ensures that a maximum surface area of the temperature control probe 130 and the outer surface 30 of the crown portion 20 are used to effect heat transfer via conduction from the temperature control probe 130 to the liquid 1005 in use. Accordingly, the rate of heat transfer from the temperature control probe 130 to the liquid 1005 in the container 1000 is increased.

In this embodiment, the convection of the liquid 1005 generated by the location of the temperature control probe 130 and the closure 10 below the liquid 1005 during heat transfer functions to increase the rate of heat transfer from the closure 10 to the liquid 1005 in the container 1000. This correspondingly increases the rate of heat transfer from the temperature control probe 130 to the closure 10 such that the overall rate of heat transfer from the temperature control probe 130 to the liquid 1005 is respectively increased.

In this embodiment, the temperature sensor allows the initial temperature of the liquid 1005 to be determined without the need for removal of the closure 10, and insertion of, for example, an external temperature measurement device such as a thermometer into the container 1000. This inhibits the liquid 1005 in the container 1000 from becoming contaminated due to, for example, contact with the external temperature measurement device. Furthermore, the temperature sensor provides user convenience, since the temperature sensor is inherent in the temperature control apparatus 200 and a separate temperature sensor that requires, for example, manual operation by the user is not required in use.

In one embodiment, the temperature sensor is adapted to provide a numerical temperature reading corresponding to the initial temperature of the liquid 1005 in the container 1000. In this instance, the user may subsequently input the numerical temperature reading to the temperature control apparatus 200 using the user input terminal 140. In another embodiment, the temperature sensor may be adapted to provide an input corresponding to the initial temperature of the liquid 1005 directly to the processor 230. Alternatively, the initial temperature of the liquid 1005 can be input by the user at the user input terminal 140 without requiring the use of the temperature sensor. For example, when the liquid 1005 to be heated is previously stored at a known storage temperature, the initial temperature of the liquid 1005 is correspondingly known and can be input directly into the user input terminal 140.

In this embodiment, the user input terminal 140 allows the temperature control apparatus 200 to be compatible for use with a range of different types and volumes of liquids 1005, since the user is able to input the one or more inputs that define the type or volume of the liquid 1005 in the container 1000 at the user input terminal 140. For example, the user is able to input the input corresponding to the specific heat capacity of the liquid 1005 such that the temperature control apparatus 200 can be used with a range of liquids 1005 with differing specific heat capacities. In a further example, the user is able to input the input corresponding to the final desired temperature of the liquid 1005 such that the temperature control apparatus 200 can be used to heat the liquid 1005 to a range of differing final desired temperatures. In other embodiments, wherein the one or more inputs are fixed, the user may not, for example, be required to enter the one or more fixed inputs. In these embodiments, the one or more pre-programmed inputs function as an alternative to the one or more inputs. For example, in the instance that the temperature control apparatus 200 is adapted for use with only one type of liquid 1005 with a known specific heat capacity, the specific heat capacity of the liquid 1005 may be stored as a pre-programmed input such that the user is not required to provide the input corresponding to the specific heat capacity of the liquid 1005 when the temperature control apparatus 200 is used.

In this embodiment, the mass measure 150 affords the user a convenient means of determining the mass of the liquid 1005 in the container 1000. In one embodiment, the mass measure 150 may be adapted to provide a numerical reading corresponding to the mass of the liquid 1005 in the container 1000. In this instance, the user may subsequently input the numerical reading to the temperature control apparatus 200 using the user input terminal 140. In another embodiment, the mass measure 150 may be adapted to provide an input corresponding to the mass of the liquid 1005 directly to the processor 230. In yet other embodiments, the temperature control apparatus 200 may be, for example, adapted for use with only one type of liquid 1005 with a specified volume. In such embodiments, the mass of the liquid 1005 may be further stored as a pre-programmed input such that the mass of the liquid 1005 is not required to be determined by the mass measure 150 or input by the user.

In this embodiment, the temperature control apparatus 200 uses the output value to cause the power source 135 to provide the corresponding specified amount of energy to the temperature control probe 130 such that the temperature control probe 130 generates the corresponding specified amount of heat energy, respectively. This is a feed forward control system. In some embodiments a temperature sensor feeds back to the controller from a temperature sensor, but in preferred embodiments and in those shown in the Figures there is no feedback from any temperature sensor. This further inhibits the temperature of the temperature control probe 130 from increasing above the preset maximum temperature, since the temperature of the temperature control probe 130 is controlled, in this embodiment, by the specified amount of heat generated by the temperature control probe 130. This is beneficial in making the temperature control apparatus 200 safe for use since the temperature of the temperature control probe 130 will not exceed the preset maximum temperature in use. This is further beneficial, for example, in making the temperature control apparatus 200 suitable for use with heat sensitive liquids 1005.

In one embodiment, the output value is calculated as a function of the initial temperature of the liquid 1005, the final desired temperature of the liquid 1005, the specific heat capacity of the liquid 1005, the mass of the liquid 1005, and the heat loss correction factor. In this embodiment, the heat loss correction factor functions to allow the output value to take into consideration external factors such as heat loss to the surroundings from, for example, the temperature control probe 130 and the container 1000 during heat transfer, in use. Furthermore, the heat loss correction factor also functions to allow the output value to take into consideration system factors such as heat generation efficiency of, for example, the temperature control probe 130, and energy transfer efficiency from, for example, the power source 135 to the temperature control probe 130. In one embodiment, the heat loss correction factor is determined from experiments conducted at, for example, a combination of a range of different atmospheric conditions (for instance, atmospheric temperature and wind speed). Correspondingly, a range of different heat loss correction factors may be derived from the experiments for use in the respective combination of atmospheric conditions. In another embodiment, the temperature control apparatus 200 further comprises an atmospheric temperature sensor (not shown) located to measure the temperature of the atmosphere immediately surrounding the temperature control apparatus 200, in use. In this embodiment, the processor 230 is further adapted to calculate the heat loss correction factor as a function of the atmospheric temperature. In yet another embodiment, the output value is calculated as a function of the initial temperature, the final desired temperature, the specified heat capacity and the mass of the liquid 1005 in the container 1000. For example, when the heat loss from the temperature control probe 130 is negligible such as when the temperature control apparatus 200 is well insulated, the heat loss correction factor is not required in the calculation of the output value.

One of the advantages of the present invention is that the closure 10 functions both as a heat transfer device that enables heat to be transferred from the temperature control probe 130 to the liquid 1005 in the container 1000, and as a cap for sealing the liquid 1005 in the container 1000 for purposes other than heat transfer, such as storage or transport of the liquid 1005. Sealing the liquid 1005 in the container 1000 is further beneficial, for example, in preventing spillage of the liquid 1005 during heating. As a result of the liquid 1005 being sealed, it is possible, for example, to substantially orient the container 1000 such that the closure 10 is below the container 1000, and correspondingly, the liquid 1005 is located above the closure 10 in use. This ensures that the liquid 1005 makes contact with the closure 10 even when the container 1000 is not completely filled by the liquid 1005. Additionally, having the liquid 1005 located above the closure 10 enables more convection within the liquid 1005 than, for example, having the liquid 1005 located below the closure 10 during heat transfer, in use. Convection increases the rate of heat transfer from the closure 10 to the liquid 1005, and further inhibits inadvertent overheating of the liquid 1005 in contact with the second surface area 25 of the crown portion 20 during heat transfer.

Advantageously, the crown portion 20 of the closure 10 allows the liquid 1005 in the container 1000 to be heated without the need for prior removal of the closure 10, and insertion of, for example, an external heat transfer device into the container 1000. This inhibits the liquid 1005 in the container 1000 from becoming contaminated due to, for example, contact with the external heat transfer device. This is further beneficial in affording user convenience since the closure 10 does not need to be removed, for example, until the liquid 1005 in the container 1000 is heated and ready to be used.

In this embodiment, the direct contact between the second surface area 25 of the crown portion 20 of the closure 10 and the liquid 1005 improves the efficiency of heat transfer from the closure 10 to the liquid 1005.

A further advantage of preferred embodiments of the present invention is that the crown portion 20 may be removed from the overcap 15 such that the crown portion 20 and the overcap 15 can be subjected to separate treatments, (for instance, sterilization) or can be disposed of separately. Advantageously, the crown portion 20 and the overcap 15 may be made from different materials according to their respective functions. For example, the crown portion 20 may be made from one or more materials with good thermal conductivity such that the crown portion 20 may transfer heat efficiently and promptly, and the overcap 15 may be made of one or more materials with good sealing properties and good temperature resistance such that the overcap 15 may effectively seal the liquid 1005 in the container 1000, and further be cool to the touch immediately after heat transfer, respectively.

In this embodiment, the one or more projections 35 increase the total heat transfer surface area. Advantageously, the rate of heat transfer, being directly proportional to the total heat transfer area, is correspondingly increased. This is beneficial, for example, in instances wherein the liquid 1005 to be heated may not be subject to a large temperature gradient that will increase the rate of heat transfer during the heat transfer process. An example of such a liquid 1005 is milk, wherein the proteins or other nutrients contained in the milk may be denatured when the liquid 1005 is exposed to high temperatures for a period of time, such as that in excess of 65° C. to 70° C. In these instances, the increased total heat transfer surface area aids in minimising the time taken for the liquid 1005 to be heated.

Advantageously, the tamper evident portion allows the integrity of the liquid 1005 in the container 1000 to be guaranteed. This is particularly beneficial where the closure 10 and container 1000 containing a single use liquid 1005 such as, for example, a pre mixed baby milk, are packaged for sale for the purpose of being disposable after use.

A further advantage of preferred embodiments of the present invention is that the use of one or more non-corroding materials in the manufacture of the closure 10 inhibits contamination of the liquid 1005 in the container 1000. Advantageously, the one or more food grade materials further prevent contamination of the liquid 1005 in the container 1000. Additionally, the use of one or more flexible materials in the manufacture of the crown portion 20 allows the crown portion 20 to better conform to the temperature control probe 130 during heat transfer in some instances, in use. This is beneficial, for example, in ensuring a good contact is maintained between the crown portion 20 and the temperature control probe 130 such that heat can be effectively conducted from the temperature control probe 130 to the crown portion 20, and heat loss from the temperature control probe 130 to, for example, surrounding air, can be correspondingly minimized. Furthermore, the use of one or more materials that are able to create a seal in the manufacture of the overcap 15 ensures that the overcap 15 is able to seal the liquid 1005 in the container 1000.

In this embodiment, the temperature control apparatus 200 allows the liquid 1005 in the container 1000 to be heated by heat transfer from the temperature control probe 130 to the outer surface 30 of the crown portion 20 of the closure 10, without the need for prior removal of the closure 10, and insertion of, for example, an external heat transfer device into the container 1000. This inhibits the liquid 1005 in the container 1000 from becoming contaminated due to, for example, contact with the external heat transfer device.

Advantageously, the amount of heat being transferred to the liquid 1005 in use is controlled by the specified amount of heat energy generated by the temperature control probe 130, and the specified amount of energy provided by the power source 135, respectively. Furthermore, the full and direct contact of the temperature control probe 130 with the outer surface 30 of the crown portion 20, in use, ensures that most of the heat generated is substantially transferred to the outer surface 30 of the crown portion 20 and correspondingly, the amount of heat loss from the temperature control probe 130 to, for example, surrounding air is minimized. Furthermore, the full and direct contact of the temperature control probe 130 with the outer surface 30 of the crown portion 20, in use, ensures that a maximum surface area of the temperature control probe 130 and the outer surface 30 of the crown portion 20 are used to effect heat transfer via conduction from the temperature control probe 130 to the crown portion 20.

A further advantage of preferred embodiments of the present invention is that the liquid 1005 is located above the closure 10 and the temperature control probe 130 during heat transfer, in use. This ensures that the liquid 1005 makes contact with the closure 10 even when the container 1000 is not completely filled with the liquid 1005. Additionally, having the liquid 1005 located above the temperature control probe 130 enables more convection within the liquid 1005 than, for example, having the liquid 1005 located below the temperature control probe 130 during heat transfer, in use. Convection increases the rate of heat transfer from the closure 10 to the liquid 1005, and further inhibits inadvertent overheating of the liquid 1005 in contact with the second surface area 25 of the crown portion 20 during heat transfer.

In this embodiment, the initial temperature of the liquid 1005 may be determined without the need for removal of the closure 10, and insertion of, for example, an external temperature measurement device such as a thermometer into the container 1000. This inhibits the liquid 1005 in the container 1000 from becoming contaminated due to, for example, contact with the external temperature measurement device.

Advantageously, the temperature control apparatus 200 is compatible for use with a range of different types and volumes of liquids 1005 since the input bank contains one or more pre-programmed inputs that define the type or volume of the liquid 1005 in the container 1000. Furthermore, the user is also able to input the one or more inputs that define the type or volume of the liquid 1005 in the container 1000 at the user input terminal 140.

Advantageously, the output value controls the specified amount of energy provided by the power source 135. Additionally, the heat loss correction factor allows the output value to take into consideration external factors such as heat loss to the surrounding from, for example, the temperature control probe 130 and the container 1000. Furthermore, the heat loss correction factor allows the output value to take into consideration system factors such as heat generation efficiency of, for example, the temperature control probe 130, and energy transfer efficiency of, for example, the power source 135 to the temperature control probe 130.

Figure 4:
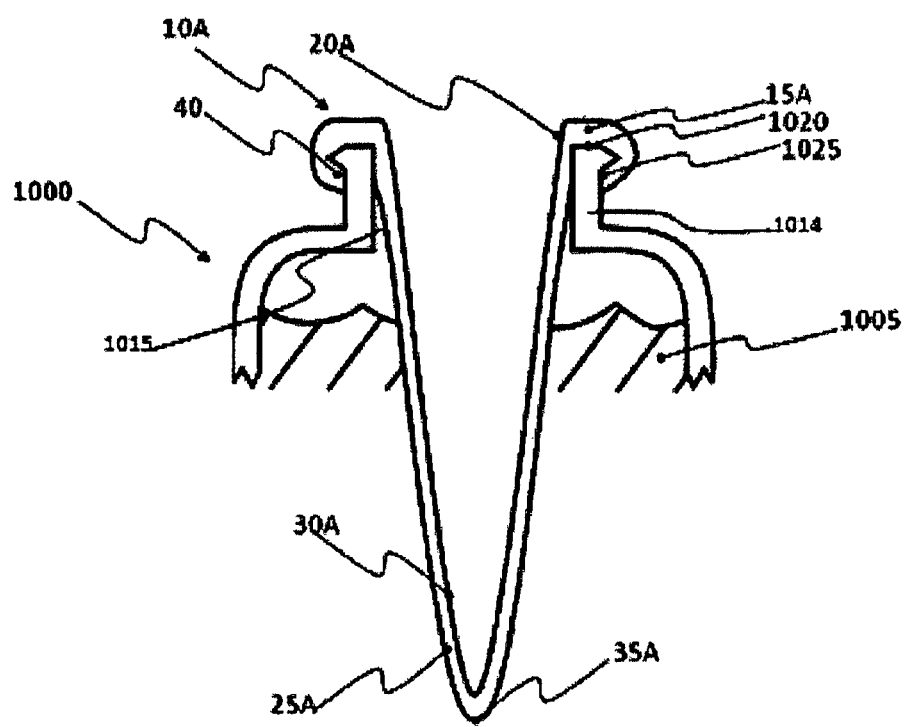
FIG. 4 is a partial sectional side elevation view of a closure for transferring heat to a liquid in a container in use, the closure comprising an engagement portion adapted to seal a rim of an opening of the container, and a crown portion in accordance with another preferred embodiment of the present invention.
Figure 5:
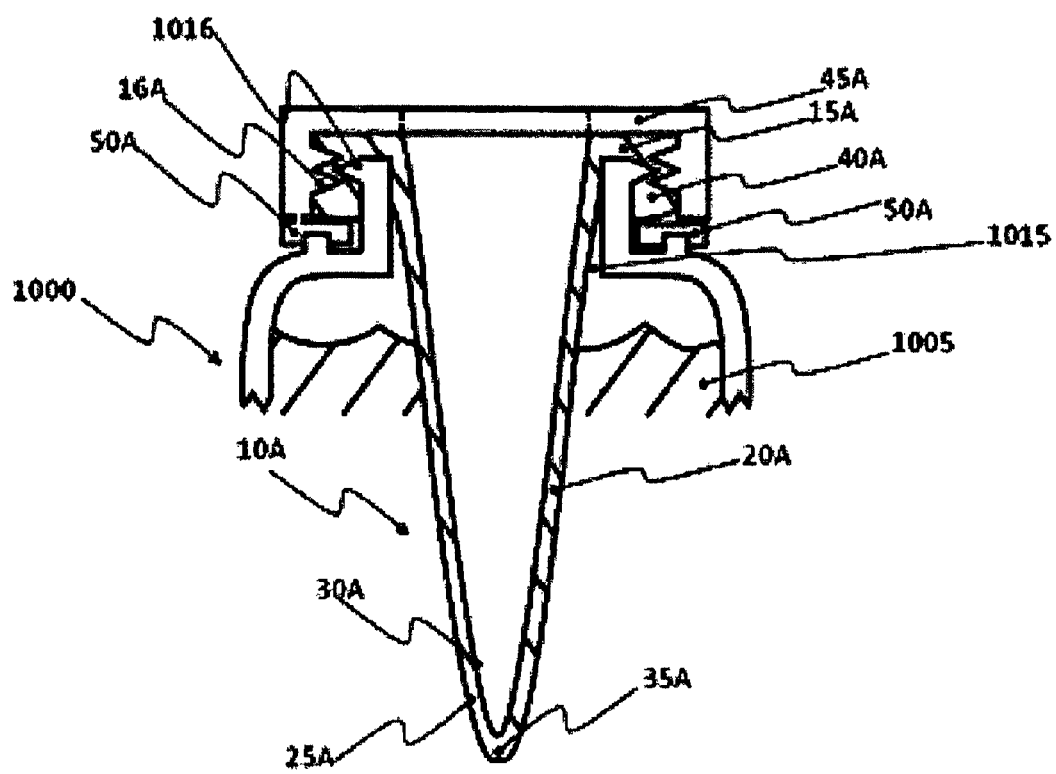
FIG. 5 is a partial sectional side elevation view of the closure and container of FIG. 4, the container being adapted to removably receive a cap having a compression ring, and wherein the engagement portion of the crown seals the rim of the container by being compressed between the compression ring and the rim when the cap is located on the container in use in accordance with another preferred embodiment of the present invention.

Referring to FIGS. 4 and 5, in accordance with another embodiment of the present invention, a closure 10A for transferring heat to a liquid 1005 in a container 1000 in use is provided. In this embodiment, the container 1000 is a baby bottle suitable for holding baby feed such as milk, that requires heating to, for example, body temperature of approximately 37° C., before being fed to a baby. In other embodiments, however, the container 1000 may be arranged for other purposes and/or to hold other liquids 1005.

In this embodiment, the closure 10A comprises an engagement portion 15A adapted to sealingly abut a rim 1020 of an opening 1015 of the container 1000 such that the liquid 1005 is sealed in the container 1000. In a preferred embodiment, the engagement portion 15A sealingly abuts the rim 1020 of the container 1000 by adhesion. In this embodiment, the engagement portion 15A may be adhered to the rim 1020 using one of a number of suitable adhesion means, including but not limited to: heat sealing or chemical adhesion. Preferably, the engagement portion 15A is removable from the rim 1020 by peeling. In another embodiment, the container 1000 is adapted to removably receive a cap 45A having a compression ring (not shown), and wherein the engagement portion 15A of the closure 10A sealingly abuts the rim 1020 of the container 1000 by being compressed between the compression ring and the rim 1020 when the cap 45A is located on the container 1000 in use. It will therefore be appreciated that the engagement portion 15A can be made to sealingly abut the rim 1020 of the container 1000 by any suitable means within the scope of the present invention. In this embodiment, preferably, the cap 45A comprises a cap engagement arrangement 16A to engage a cooperative engagement arrangement 1016 of the container 1000 immediately adjacent to the opening 1015 of the container 1000 such that the engagement portion 15A of the closure 10A is compressed between the compression ring and the rim 1020 of the container 1000. In one embodiment, the cap engagement arrangement 16A is a threaded arrangement and the cooperative engagement arrangement 1016 is a complementary thread adapted to receive the threaded arrangement. In another embodiment, the cap engagement arrangement 16A is a smooth surface and the cooperative engagement is a complementary smooth and flexible surface, such as one made of an elastomer, adapted to form a press fit with the smooth surface of the cap engagement arrangement 16A. It will therefore be appreciated that the cap engagement arrangement 16A and the cooperative engagement arrangement 1016 may take any suitable form within the scope of the present invention.

In this embodiment, the closure 10A further comprises a crown 20A being heat conductive and having a total heat transfer surface area including a outer surface 30A and a second surface area 25A such that, in use, the outer surface 30A contacts a temperature control probe 130 as described in the second embodiment of the present invention and as shown in FIG. 2, and the inner surface contacts the liquid 1005 to allow heat to be transferred from the temperature control probe 130 to the liquid 1005.

In a preferred embodiment, the crown 20A comprises one or more projections 35A that function to increase the total heat transfer surface area. In one embodiment, the one or more projections 35A are a single projection of a geometry with a large surface area to volume ratio, for example, a tetrahedron or a cube. In another embodiment, the one or more projections 35A are numerous projections of a suitable packing geometry, such as rectangular cuboid, that have a large total surface area to total volume ratio when considered together. It will therefore be appreciated that any suitable combination of the number and geometry of the one or more projections 35A to increase the total heat transfer surface area, and maximise the total surface area to total volume ratio of the one or more projections 35 is possible within the scope of the present invention.

Preferably, the closure 10A further comprises a puncturable portion (not shown) such that the liquid 1005 sealed in the container 1000 can be accessed when the puncturable portion is punctured. In one embodiment, the puncturable portion is made of a material (for instance, metal foil, metal foil with a polymer coating or simply a suitable polymer) that can be readily punctured by a sharp device such as the sharp end of a straw. It will however be appreciated that the puncturable portion may take any suitable form within the scope of the present invention.

In a preferred embodiment, the closure 10A is made from one or more materials selected from a polymer, a ceramic, a glass, a substantially non-corroding metal, or a combination thereof. Preferably, the crown 20A of the closure 10A is made from one or more materials with good thermal conductivity such as metal foil with a polymer coating or metal foil. In one embodiment, the crown 20A is made of one or more flexible materials such that the crown 20A is collapsible. The use of a collapsible crown 20A is beneficial as it enables the use of more economical materials which can be used as disposable components. In another embodiment, the crown 20A is made of one or more rigid materials such that the crown 20A is rigid. The use of a rigid crown 20A is also beneficial as it is robust and can be cleaned and reused on numerous occasions. Preferably, the engagement portion 20A is made of one or more materials that are able to create a seal. More preferably, the one or more materials used in the manufacture of the closure 10A are food grade.

Referring to FIG. 4, in a preferred embodiment, the container 1000 comprises a wall 1014 defining the opening 1015 of the container 1000, the wall 1014 having a rim region 1025 disposed adjacent to the rim 1020 and the engagement portion 15A of the closure 10A comprises a skirt portion 40 that extends beyond the rim 1020 of the container 1000 to cover the rim region 1025. In one embodiment, the skirt portion 40 is adapted to extend beyond the rim 1020 radially and fold around the rim region 1025. It will be appreciated however, that the skirt portion 40 may take any possible form within the scope of the present invention.

Referring to FIG. 5, in this embodiment, the cooperative engagement arrangement 1016 of the container 1000 may further receive one or more additional parts (not shown) adapted for use with the container 1000 to enable a teat (not shown) to be located on the container 1000. For example, the one or more additional parts may include the teat arranged on a teat holder (not shown) adapted to cooperatively engage with the container 1000 using the cooperative engagement arrangement 1016 of the container 1000. Accordingly, in this respect, the cooperative engagement arrangement 1016 can be used for coupling both the teat holder and the cap 45A to the container 1000.

Referring once again to FIGS. 4 and 5, the closure 10A functions both as a heat transfer device that enables heat to be transferred from the temperature control probe to the liquid 1005 in the container 1000, and as a seal for sealing the liquid 1005 in the container 1000 for purposes other than heat transfer such as storage or transport of the liquid 1005. Sealing the liquid 1005 in the container 1000 inhibits, for example, spillage of the liquid 1000 during heat transfer. As a result of the liquid 1005 being sealed by the closure 10A, it is possible, in this embodiment, to substantially orient the container 1000 such that the closure 10A is located below the container 1000, and correspondingly, the liquid 1005 is located above the closure 10A in use. This ensures that the liquid 1005 contacts the closure 10A even when the container 1000 is not completely filled with the liquid 1005. Additionally, having the liquid 1005 located above the closure 10A enables more convection within the liquid 1005 than, for example, having the liquid 1005 located below the heat transfer sheath 10A during heat transfer, in use. Convection increases the rate of heat transfer from the closure 10A to the liquid 1005, and further inhibits inadvertent overheating of the liquid 1005 in contact with the inner surface 25A of the crown 20A during heat transfer.

In this embodiment, the one or more projections 35A are preferably of a suitable size such that the inner surface 25A of the one or more projections 35A of the crown 20A is in full contact with the liquid 1005 when the container 1000 is not completely filled with the liquid 1005. It will be appreciated, therefore, that in such instances, a range of closures 10A with one or more suitably sized projections 35A for transferring heat could be manufactured to cater for a range of volumes of liquid 1005.

In this embodiment, the crown 20A of the closure 10A allows the closure 10A to function as a heat transfer device such that heat may be transferred from the temperature control probe 130 to the liquid 1005 in the container 1000 without the need for prior removal of the closure 10A, and insertion of, for example, an external heat transfer device into the container 1000. Therefore, a primary function of the crown 20A is to transfer heat efficiently and promptly from the temperature control probe 130 to the liquid 1005 in the container 1000. Concomitantly, the engagement portion 15A allows the closure 10A to further function as a seal for sealing the liquid 1005 in the container 1000. Therefore, a primary function of the engagement portion 15A is to ensure that a good seal is formed between the engagement portion 15A and the rim 1005 of the container 1000 by virtue of, for example, the adhesion of the engagement portion 15A to the rim 1020 or the compression of the engagement portion by the compression ring of the cap 45A and the rim 1020 of the container 1000 such that the liquid 1005 is sealed in the container 1000. As such, preferably the closure 10A is made of a material with good thermal conductivity and good sealing properties, for example, aluminium foil. Alternatively, preferably the crown 20A and the engagement portion 15A are made of different materials according to their respective functions. In this embodiment, the crown 20A is made of one or more materials with good thermal conductivity such that the crown 20A may transfer heat efficiently and promptly; and the engagement portion 15A is made of one or more materials that are able to create a seal such that the engagement portion 15A may effectively seal the liquid 1005 in the container 1000.

In this embodiment, the closure 10A and the container 1000 can be subject to separate treatments (for instance, sterilization), or can be disposed of independently. In one embodiment, the liquid 1005 is packaged for sale in the container 1000 and supplied with the closure 10A such that both the closure 10A and the container 1000 may be disposed of after a single use. In this embodiment, preferably, the engagement portion 15A of the heat transfer sheath 10A sealingly abuts the rim of the container 1000 by adhesion. Preferably, the engagement portion 15A is removable from the rim 1020 by peeling such that the liquid 1005 in the container 1000 can be accessed, for example, after being heated by heat transfer. Alternatively, the puncturable portion allows the closure 10A to be easily punctured such that a liquid retrieval device, for example, a straw may be used to access the liquid 1005 in the container 1000. Preferably, the closure 10A further comprises a tamper evident portion (not shown) adapted to, for example, tear from the closure 10A when the closure 10A is, for example, peeled from the container 1000. This allows the tamper evident portion to provide a guarantee for the integrity of the liquid 1005 in the container 1000.

In another embodiment, the closure 10A is reusable and supplied for use on a disposable container 1000. For example, the liquid 1005 can be packaged for sale in the container 1000 with a storage cap (not shown) or any other suitable sealing means. When the liquid 1005 is ready to be heated for use, the storage cap is replaced with the closure 10 such that heat can be transferred to the liquid 1005 in the container 1000. In this embodiment, the engagement portion 15A of the closure 10A sealingly abuts the rim 1020 of the container 1000 by being compressed between the compression ring and the rim 1020 of the container 1000. After use, the container 1000 and the storage cap can be disposed of while the closure 10A and the cap 45A are sterilized for further use.

In yet another embodiment, the closure 10A, the container 1000 and cap 45A are all disposable after a single use. In this embodiment, preferably, the liquid 1005 is packaged for sale in the container 1000 and supplied with the closure 10A and the cap 45A, with the liquid 1005 being sealed in the container 1000 by the closure 10A. In this embodiment, preferably, the cap 45A further comprises a cap tamper evident portion 50A as shown in FIG. 5. In this embodiment, the cap tamper evident portion 50A is adapted to for example, tear from the cap 45A when the cap 45A is initially removed from the container 1000. This is particularly beneficial where the closure 10A and container 1000 containing a single use liquid 1005 such as, for example, a pre mixed baby milk, are packaged for sale for the purpose of being disposable after use.

In this embodiment, the one or more projections 35A function to increase the total heat transfer surface area, and to correspondingly increase the rate of heat transfer from the temperature control probe 130 to the liquid 1005. The increased surface area to volume ratio of the one or more projections 35A further increases the rate of heat transfer from the temperature control probe 130 to the liquid 1005. The large total heat transfer surface area is particularly significant, for example, in instances when the liquid 1005 to be heated may not be subject to a large temperature gradient to increase the rate of heat transfer during the heat transfer process. An example of such a liquid 1005 is milk, wherein the proteins or other nutrients contained in the milk may be denatured when the liquid 1005 is exposed to high temperatures for a period of time, such as temperatures in excess of approximately 60° C. to 70° C. In these instances, the increased total heat transfer surface area aids in minimising the time taken for the liquid 1005 to be heated.

In this embodiment, the use of non-corroding and food grade materials in the manufacture of the closure 10A inhibits contamination of the liquid 1005 in the container 1000 in use. In one embodiment, the use of one or more flexible materials in the manufacture of the closure 10A ensures that a good seal can be created between the closure 10A and the rim 1020 to effectively seal the liquid 1005 in the container 1000, and that the closure 10A can be easily removed by peeling. In one embodiment, the use of one or more flexible materials in the manufacture of the crown 10A allows the crown 10A to better conform to the temperature control probe 130 during heat transfer, in use. This is beneficial, for example, in ensuring a good contact is maintained between the crown 20A and the temperature control probe 130 such that heat can be effectively conducted from the temperature control probe 130 to the crown 20A, and heat loss from the temperature control probe 130 to, for example, surrounding air, can be correspondingly minimized. In another embodiment, the use of one or more rigid materials in the manufacture of the crown 20A allows the crown 20A to better contact the temperature control probe 130. It will be appreciated, therefore, that any suitable type of material may be used to ensure that a good contact is achieved between the crown 20A and the temperature control probe 130.

Referring to FIG. 4, in this embodiment, the skirt portion 40 of the closure 10A functions to cover the rim region 1025 until the closure 10A is removed. This inhibits the rim region 1025 from being contaminated during, for example, storage and transport of the liquid 1005 such that when the liquid 1005 in the container 1000 is, for example, to be consumed directly from the container 1000 after heating, the rim region 1020 which comes into contact with, for example, the mouth remains clean.

Figure 6:
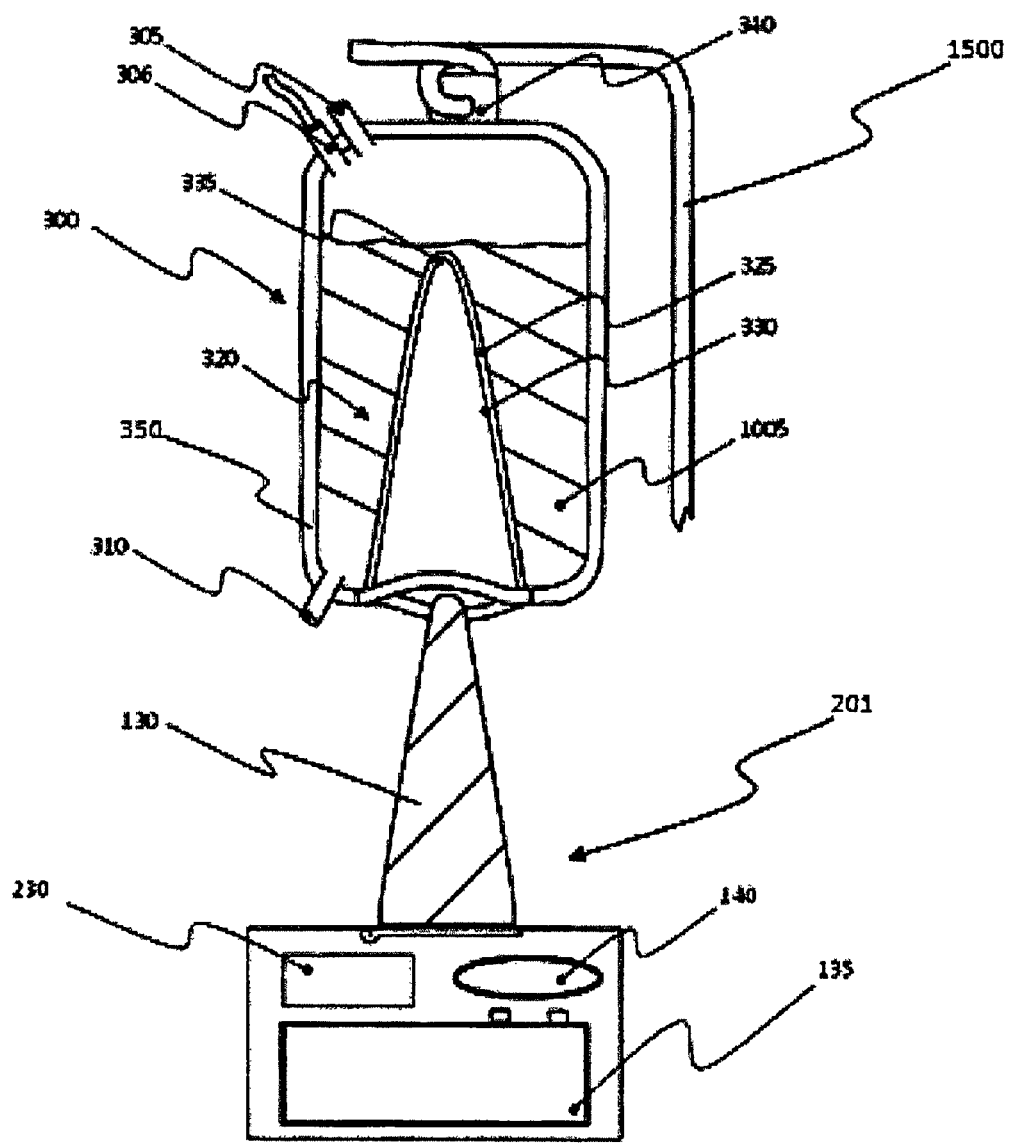
FIG. 6 is a side elevation section view of a temperature control apparatus for controlling the temperature of a liquid from an initial temperature to a final desired temperature in accordance with another preferred embodiment of the present invention, the temperature control apparatus comprising a container in sectional side view, for containing the liquid, and the temperature control unit of FIG. 2, the container comprising a wall being conductive and having a total heat transfer surface area including an inner surface and an outer surface such that, in use, the outer surface contacts the temperature control probe of the temperature control apparatus and the inner surface area contacts the liquid to allow heat to be transferred from the temperature control probe to the liquid, and a remaining region.
Figure 7:
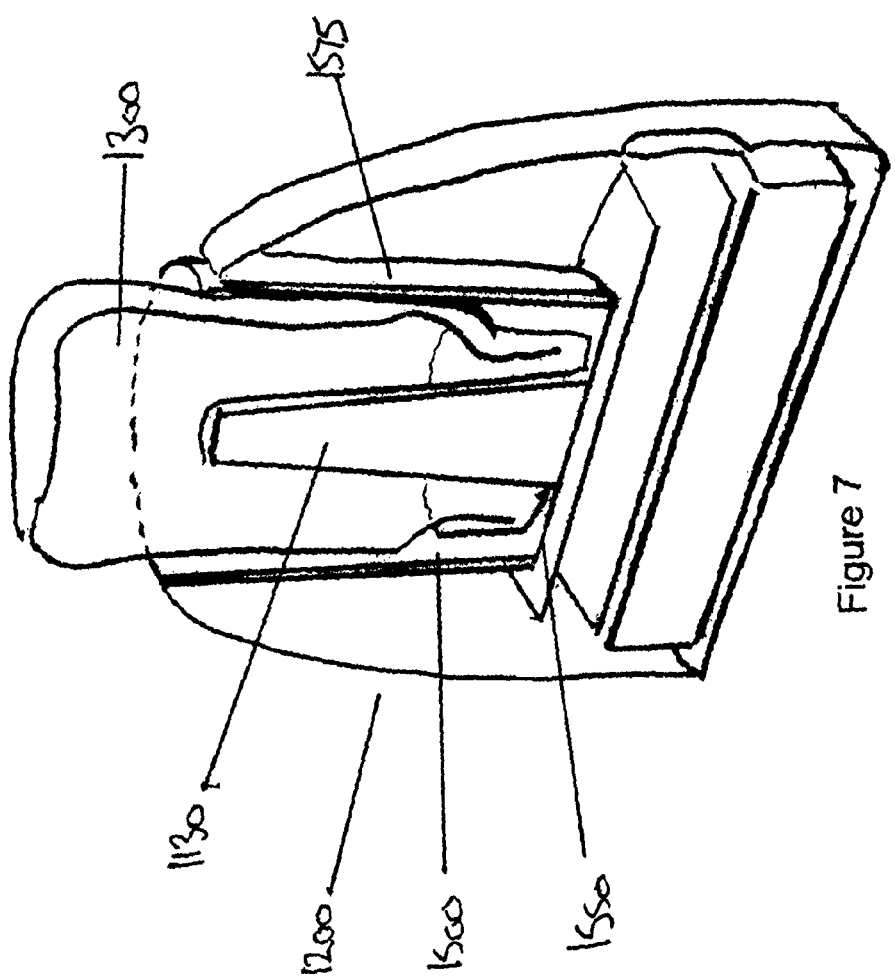
FIG. 7 is a perspective cutaway view of a temperature control apparatus in accordance with another embodiment of the present invention with a bottle docked in a dock of the apparatus for heating of liquid inside.

According to a yet further aspect of the present invention, a method of heating a liquid 1005 in a container designated as 1000 or 300 or 1300 in FIGS. 2, 6 and 7 respectively, from an initial temperature to a final desired temperature is provided. In this embodiment, the method comprises the following steps:
determining the initial temperature of the liquid 1005; and generating the amount of energy required in the form of heat to raise the temperature of the liquid 1005 to the final desired temperature.

The method of the preferred embodiments shown includes the steps of providing one or more of the following calculation data:
i. the final desired temperature of the liquid 1005 in the container 1000 or 300;
ii. a specific heat capacity of the liquid 1005 in the container 1000 or 300;
iii. a mass of the liquid 1005 in the container 1000 or 300; and
iv. a heat loss correction factor;
and calculating an amount of energy required to heat the liquid 1005 to the final desired temperature as a function of the initial temperature and the calculation data.

Preferably, the one or more of the final desired temperature of the liquid 1005, the specific heat capacity of the liquid 1005, the mass of the liquid 1005 and the heat loss correction factor are input by a user.

In this embodiment, the amount of energy generated in the form of heat to raise the temperature of the liquid 1005 to the final desired temperature corresponds to the amount of energy calculated as required to heat the liquid 1005 to the final temperature. This functions to prevent the temperature of the liquid 1005 from increasing above the final desired temperature in use.

In this embodiment, the heat loss correction factor allows the method to take into consideration external factors such as heat loss to the surroundings from, for example, the container 1000 or 300 in use.

In this embodiment, the method is compatible for use with a range of different types of liquids 1005 since the user is able to input the specific heat capacity of the liquid 1005 that defines the type of the liquid 1005 in the container 1000 or 300. Additionally, the method is also compatible for use with a range of different volumes of liquids 1005 since the user is able to input the mass of the liquid 1005 that defines the volume of liquid 1005 in the container 1000. Furthermore, the method can be used to heat the liquid 1005 to a range of final desired temperatures since the user is able to input the final desired temperature of the liquid 1005.

A first advantage of preferred embodiments of the present invention is that the method is suitable for use with heat sensitive liquids 1005 since the temperature of the liquid 1005 is prevented from increasing above the final desired temperature. Advantageously, this also avoids energy wastage.

A further advantage of preferred embodiments of the present invention is accuracy, since the heat loss correction factor allows the method to take into consideration external factors such as heat loss to the surroundings from, for example, the container 1000 or 300 in use.

Advantageously, the method is compatible for use with a range of different types and volume of liquids 1005. Furthermore, the method can be used to heat the liquid 1005 to a range of final desired temperatures.

Referring to FIG. 6 there is shown a temperature control apparatus generally indicated at 200. The temperature control apparatus is adapted to heat and cool a fluid in a bag 300. Each bag 300 includes a wall which is adapted to be invaginated by a temperature control probe 130 so that the fluid inside, in this case blood, may be heated.

The bag 300 includes a window of closure material 320 which may be a flexible and stretchable membrane 325 or a substantially rigid membrane. The membrane may include a projection 335 so as to improve the surface area of contact with the blood. The bag includes inlet and outlet ports 305, 306, 310 and an eye 340 hangs from a hook. This is so that warmed blood can be used straight away, even while it is being heated or kept warm on the temperature control apparatus 200.

In operation the temperature control probe 130 may be forced into the bag if the wall or window is a membrane (the whole wall may simply be flexible and pushed out of the way in one suitable embodiment) so as to create an invagination in the bag 300. Alternatively the invagination may be pre-formed such that a rigid material 335 such as for example stainless steel or other polymer may form a closed hole to receive the probe 130.

Figure 8:
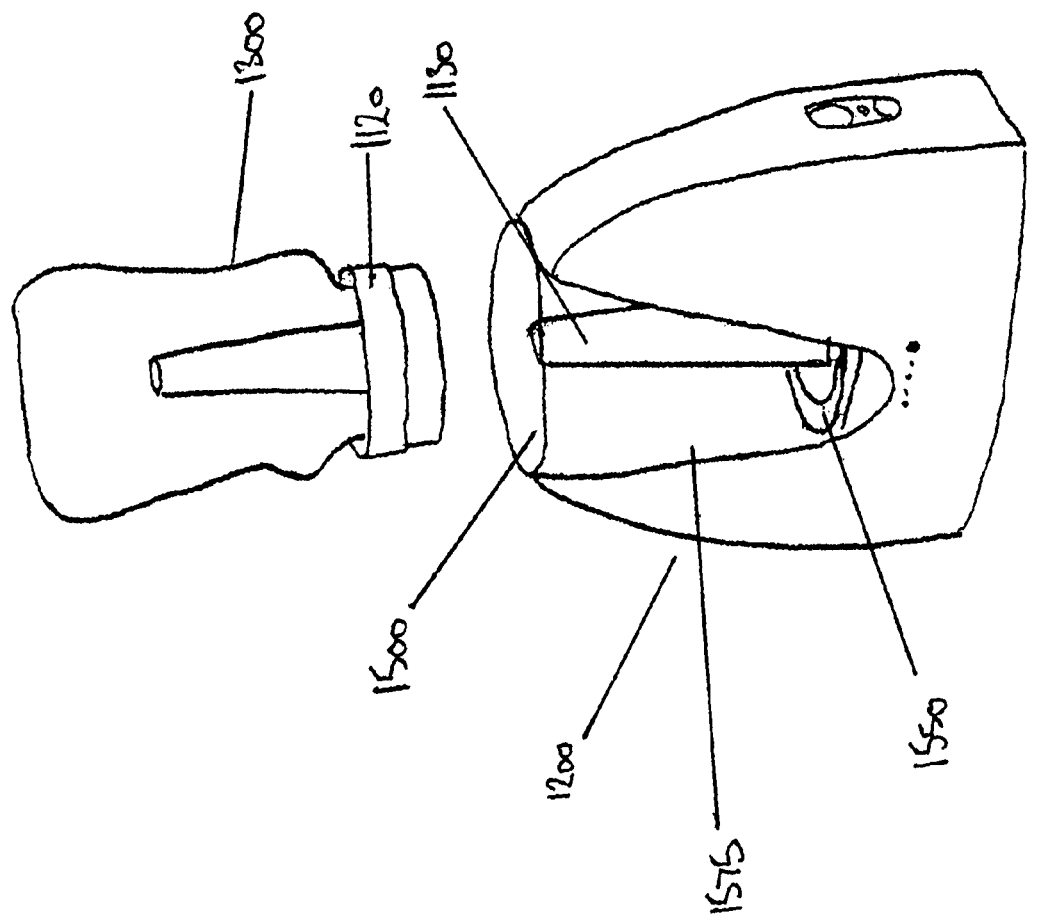
FIG. 8 is a perspective view of the temperature control apparatus of FIG. 7 showing the bottle preparing for docking in the dock, on the temperature control probe.

Referring to FIGS. 7 and 8 there is shown a temperature control apparatus generally indicated at 1200. The temperature control apparatus is adapted to heat and cool a fluid in a bottle 1300. The bottle 1300 may be as above described and is adapted to sit inverted in a dock 1500. One or more temperature control probes 1130 extend upwardly from a dock base 1550 and are adapted to either create an invagination (if the closure 1120 is a flexible, stretchable membrane) in the closure or simply fit into a substantially pre-formed invagination in the closure 1120. The heat from the temperature control probe 1130 is then rapidly transferred into the liquid since the heat source is effectively inside the bottle and has a high surface area. The walls of the dock 1575 may also include heating elements to heat the bottle. The dock walls may also be filled with a heated fluid, or other heating elements may be placed around the dock walls to improve heat transfer.

The dock may also be adapted to receive a plurality of blood bags 300 or other blood containers for heating by the one or more temperature control probes 130. This is advantageous because the bags or containers 300 may be placed into the dock around the one or more temperature control probes 130 for rapid and controlled heating by the temperature control probe 130 and/or dock walls. The bags may still be operatively connected to inlets and outlets.

Figure 9:
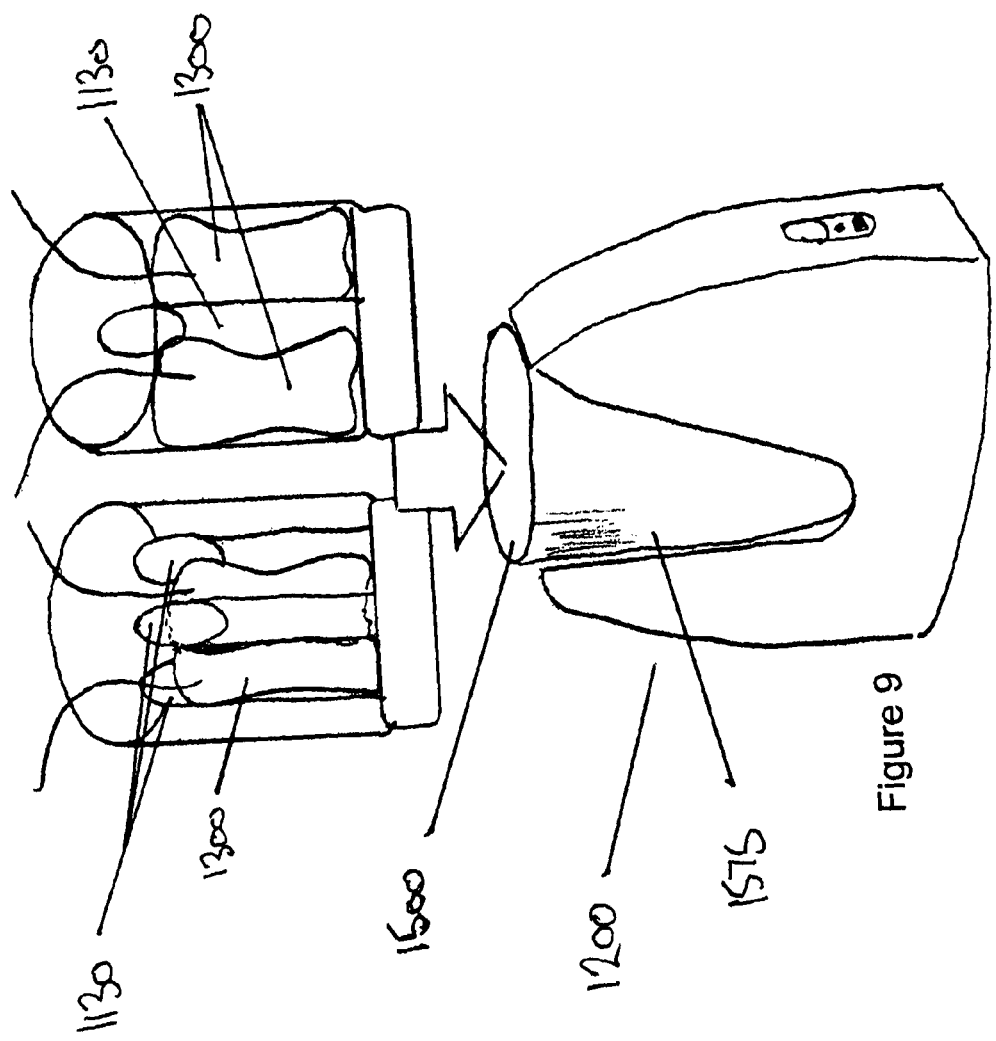
FIG. 9 is another perspective view of the temperature control apparatus of FIG. 7 which shows blood or blood products bags being warmed or cooled by the temperature control apparatus by being placed in a container which includes one or more temperature probes.

FIG. 9 shows blood or blood products bags which are inserted or dropped into the dock which in this case can be considered a container 1500. The dock itself 1500 includes one or more temperature control probes 1130 (three on the left dock and one on the right dock) which may heat or cool the blood bags 1300 or blood bag equivalents without any contact between the one or more temperature control probes 1130 and the blood contents themselves in the blood bags 1300. FIG. 9 is illustrative and a similar device can heat or cool two or more blood bags or blood bag equivalents 1300. If, for example, three blood bags 1300 are to be heated, one blank bag may be held in the dock with the other three blood bags for even heating of the blood bags.

Definitions

Unless specifically stated otherwise, as apparent from the following discussions, it is appreciated that throughout the specification discussions utilizing terms such as "processing", "computing", "calculating", "determining", "analysing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory.

A "computer" or a "computing device" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. The processing system further may include a memory subsystem including main RAM and/or a static RAM, and/or ROM.

Furthermore, some of the embodiments are described herein as a method or combination of elements of a method that can be implemented by a processor of a processor device, computer system, or by other arrangement of carrying out the function. Thus, a processor with the necessary instructions for carrying out such a method or element of a method forms an arrangement for carrying out the method or element of a method. Furthermore, an element described herein of an apparatus embodiment is an example of an arrangement for carrying out the function performed by the element for the purpose of carrying out the invention.

Reference throughout this specification to "one embodiment" or "an embodiment" is to be taken to mean that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but that may be so. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is to be understood that embodiments of the invention may be practiced without these specific details. In other instances, well-known methods, structures and techniques have not been shown in detail in order not to obscure an understanding of this description.

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also arrangement including at least the elements/features that follow the term, but not excluding others. Thus, including is synonymous with and arrangement comprising.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added to methods described within the scope of the present invention.

Although the invention has been described with reference to specific examples, it will be appreciated by those skilled in the art that the invention may be embodied in many other forms.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A system for heating or cooling the contents of a container, the system comprising:
    a container configured to hold a liquid, the container having one opening region;
    a closure to close the opening region of the container, the closure comprising:
        an engagement portion to sealingly engage the opening region of the container;
        a removable crown portion defining a recess extending into an inner region of the container via the opening region, the recess having an inner surface and an outer surface opposed to the inner surface, such that in use the inner surface is in fluid communication with contents of the container and the outer surface receives a temperature control probe to facilitate heat transfer to or from contents of the container by the temperature control probe, the crown portion attached to or integral with the engagement portion;
    an overcap configured to engage with the opening region of the container and to secure the crown portion to the container, the overcap including an access aperture so that the crown portion is accessible to the temperature control probe without removing the overcap; and
    a dock configured to receive the container, the dock comprising:
        the temperature control probe configured to engage with the recess of the crown portion on the container; and
        a temperature controller operatively connected to the temperature control probe, such that the temperature controller controls the temperature of the temperature control probe to heat or cool contents of the container via the recess without the probe contacting the contents of the container.

2. The system of claim 1 wherein the crown portion comprises a resilient material.

3. The system of claim 2 wherein the resilient material comprises a membrane having a thickness of about 0.5 mm to 10 mm.

4. The system of claim 1 wherein the crown portion comprises a substantially rigid material so that the crown portion extends into the inner region of the container.

5. The system of claim 1 wherein the crown portion includes one or more projections increasing a surface area for facilitating heat transfer between contents of the container and the crown portion by the temperature control probe.

6. The system of claim 1 wherein the dock includes a dock base and the temperature control probe extends upwardly from the dock base.

7. The system of claim 6 wherein the dock includes two or more temperature control probes.

8. The system of claim 1 further comprising a temperature sensor to sense an initial temperature of a liquid in the container prior to control of the temperature of the liquid.

9. The system of claim 1 further comprising a user input terminal to receive user inputs including inputs selected from the group consisting of: a final desired temperature of the liquid, a specific heat of the liquid, a weight of the liquid in the container, and a maximum permissible liquid temperature.

10. The system of claim 9 having a processor adapted to calculate an output energy required to obtain a final desired temperature of the liquid based on user inputs to the user input terminal.

11. The system of claim 1 further comprising a sensor to sense the weight of the liquid in the container.

12. The system of claim 1 further comprising a power source.

13. A method of heating or cooling the contents of a container, the method comprising the steps of:
    adding a liquid to a container having one opening region;
    closing the container with a closure configured to close the opening region of the container, the closure comprising:
        an engagement portion to sealingly engage the opening region of the container;
        a removable crown portion defining a recess extending into an inner region of the container via the opening region, the recess having an inner surface and an outer surface opposed to the inner surface, whereby in use the inner surface is in fluid communication with liquid in the container and the outer surface receives a temperature control probe to facilitate heat transfer to or from liquid in the container by the temperature control probe the crown portion attached to or integral with the engagement portion; and
        an overcap configured to engage with the opening region of the container and to secure the crown portion to the container, the overcap including an access aperture so that the crown portion is accessible to the temperature control probe without removing the overcap;
    mounting the container containing the liquid in a dock to receive the container, the dock comprising:
        the temperature control probe configured to engage with the recess of the crown portion on the container; and
        a temperature controller operatively connected to the temperature control probe, the temperature controller controls the temperature of the temperature control probe to heat or cool liquid in the container via the recess without the probe contacting the liquid in the container; and heating or cooling the liquid in the container using the temperature controlled probe positioned in the recess of the crown portion.

14. The method of claim 13 further comprising the steps of:

measuring an initial temperature of liquid in the container;

obtaining one or more of the following data:
   i. the final desired temperature of the liquid in the container;
   ii. a specific heat capacity of the liquid in the container;
   iii. a weight of the liquid in the container;
   iv. a heat loss correction factor; and calculating an amount of energy required to heat or cool the liquid to the desired temperature as a function of the initial temperature and one or more of the data of i to iv.

* * * * *